US008389678B2

(12) United States Patent
Hoey et al.

(10) Patent No.: US 8,389,678 B2
(45) Date of Patent: Mar. 5, 2013

(54) **PROTEIN FRAGMENTS OF VIRB10 AND SERO-DETECTION OF *ANAPLASMA PHAGOCYTOPHILUM***

(75) Inventors: John G. Hoey, Elmer, NJ (US); Denise P. Dimitrov, Marlton, NJ (US); Lisa B. Huang, Princeton, NJ (US); Martin E. Adelson, Belle Mead, NJ (US); Eli Mordechai, Robbinsville, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

(21) Appl. No.: 13/418,567

(22) Filed: Mar. 13, 2012

(65) Prior Publication Data

US 2012/0183979 A1 Jul. 19, 2012

Related U.S. Application Data

(62) Division of application No. 12/658,506, filed on Feb. 9, 2010, now Pat. No. 8,283,130.

(60) Provisional application No. 61/208,761, filed on Feb. 27, 2009.

(51) Int. Cl.

| | |
|---|---|
| *A61K 38/00* | (2006.01) |
| *A61K 39/02* | (2006.01) |
| *C12N 15/09* | (2006.01) |
| *C12P 29/04* | (2006.01) |

(52) U.S. Cl. ........ 530/300; 530/811; 530/324; 530/825; 530/806; 435/69.3; 435/71.1; 435/975; 514/1.1; 424/190.1; 424/234.1

(58) Field of Classification Search ........................ None
See application file for complete search history.

(56) References Cited

PUBLICATIONS

Ohashi et al. Infect. Immun. 70: 2128-2138, 2002.*
Sambrook et al. Molecular Cloning, A Laboratory Manual, Second Edition, Cold Spring Harbor, pp. 17.1-17.44, 1989.*
Campbell AM. In: Monoclonal Antibody Technology. Elsevier Science Publishers, The Netherlands, Chapter 1, pp. 1-32, 1984.*

* cited by examiner

*Primary Examiner* — S. Devi
(74) *Attorney, Agent, or Firm* — Siu K. Lo

(57) ABSTRACT

Disclosed are cloning and expression of a plurality of protein fragments of virB10, a Type IV Secretion System (TIVSS) in *Anaplasma phagocytophilum*. Such recombinant protein fragments are useful in the ELISA detection of *anaplasma* pathogen. The use of same as kits for ELISA is also disclosed.

11 Claims, 39 Drawing Sheets

Figure 5

TIVSS virB10
Nucleotide Sequence (SEQ ID No. 10)

```
   1 ATGGCTGACG AAATAAGGGG TTCTAGCAGC GGGGAGAACA TTGAGGATAA
  51 TGTTAATGTA GTAGGTGTAG CAAAGAGTAA GAAGCTCTTT GTTATCATAG
 101 TGGTGCTGAT TGCTACTGGA CTTATGTACT ATTTTTTCTT CTTCAATAAG
 151 GAGTCTTCGG ATAATGAGGA AGATACTCAG ATTCCTCGTG TTATCGAAGA
 201 GAAGGAAGTA GAAAAATTGA GGAAGGATGC GGGAAGGCCG GCTCAGGAGA
 251 CTGCTCCTAG AATCTTGACG CCACCACCGA GGTTGCCTGA GTTGCCGCCG
 301 CTTGTAATGC CTACTGTACC TGATATTCCT GTGGTAACAA AATTGCTTAA
 351 GCCGCCTGTA GAGGAGGAGT TTGTTGAAGA GTATAACGTT CAAGAGGTTC
 401 CTTCACCAAT GGGTAATATT GCTCCTCCTG AACGCGAGGA GATATCTTTA
 451 CCTTTGCCGT ATAAGACGAT AACAACTGAG CAGCCGTCGT TTCTGGGGTA
 501 TGATAAAGAA AAAAGAGGAG CCCCTATGAT CGCATTTGGT GGCGGTGGTG
 551 GCGAAGCTGC TGGTAGTGAA TCCGGTGATG GTTCTGTTGG CGGGAAGGAA
 601 GATGCTCGGT TTACTGCGTG GCAAGGGTTA GAGGGTACTC AATCTCCTAG
 651 TGTTAGAGCG ACAAGAGTGG GGGATACGAG ATATATAATA CTGCAAGGTC
 701 ACATGATTGA TGCTGTTTTA GAGACAGCAA TAAACTCGGA TATTTCAGGG
 751 GTGCTCAGGG CTGTGGTATC CAGAGATGTA TATGCTTCTT CTGGAGATGC
 801 GGTTGTAATA CCGAAGGGGT CTAGGCTTAT TGGTAGTTAT TTCTTTGATT
 851 CTGCTGGTAA CAATGTAAGG GTTGATGTTA ATTGGTCCAG GGTCATTTTA
 901 CCTCATGGCG TTGATATACA GATAGCGTCT AGTGGAACTG ATGAACTAGG
 951 AAGAAATGGT ATTTCTGGTG TTGTAGATAA TAAAGTGGGC TCCATATTGA
1001 CCTCTACTAT CTTTTTGGCG GGTATATCTT TGGGGACAGC TTATGTGACC
1051 GAGCAGATAC CGTCGTTGCG GACTGAGACT GTTAAGGTTG AGACTCCTGC
1101 GGATGGTAAA GACGGGAAGA AAACTACTTC ATCATCTCTT TCAACAAAGA
1151 TAGTTTCTGA TGCTATTAAG GATTTCTCTG ACTCTATGAA AGAGATTGTG
1201 AATAAGTATT CTAATAGGAC TCCGACTGTC TATGTAGATC AGGGTACTGT
1251 GATGAAGGTA TTTGTGAATC AGGACGTAGT ATTTCCTCGT GATGCGGTGA
1301 GGTAG
```

Deduced Amino Acid Sequence (SEQ ID No. 11)

```
MADEIRGSSSGENIEDNVNVVGVAKSKKLFVIIVVLIATGLMYYFFFFNK  50
ESSDNEEDTQIPRVIEEKEVEKLRKDAGRPAQETAPRILTPPPRLPELPP 100
LVMPTVPDIPVVTKLLKPPVEEEFVEEYNVQEVPSPMGNIAPPEREEISL 150
PLPYKTITTEQPSFLGYDKEKRGAPMIAFGGGGEAAGSESGDGSVGGKE  200
DARFTAWQGLEGTQSPSVRATRVGDTRYIILQGHMIDAVLETAINSDISG 250
VLRAVVSRDVYASSGDAVVIPKGSRLIGSYFFDSAGNNVRVDVNWSRVIL 300
PHGVDIQIASSGTDELGRNGISGVVDNKVGSILTSTIFLAGISLGTAYVT 350
EQIPSLRTETVKVETPADGKDGKKTTSSSLSTKIVSDAIKDFSDSMKEIV 400
NKYSNRTPTVYVDQGTVMKVFVNQDVVFPRDAVR*
```

Colony PCR of virB10 transformants in NovaBlue *E. coli* (amplified with Ek/LIC primers)

Colony PCR of virB10 Transformants in BL21 (DE3) *E. coli* for Expression:
(amplified with vector-specific primers)

Figure 11
IgM and IgG ELISAs for recombinant virB10
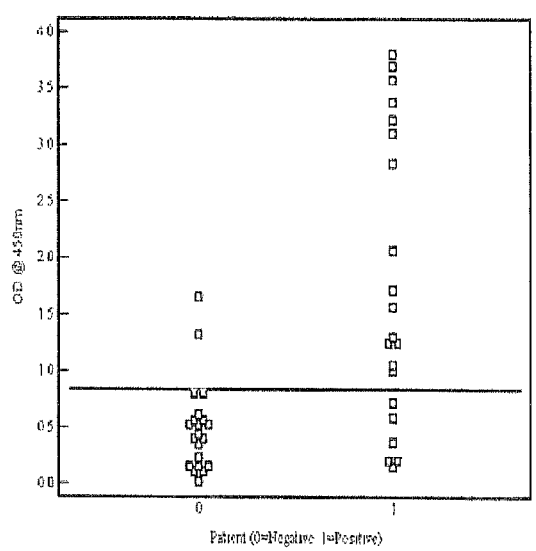
virB10 IgM ELISA
Sensitivity= 71.4%
Specificity= 90.5%
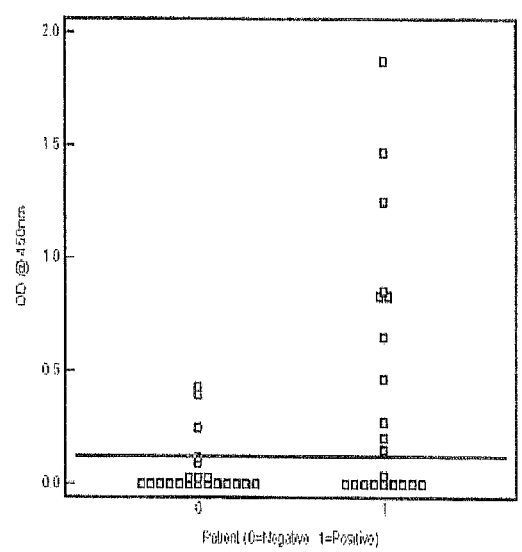
virB10 IgG ELISA
Sensitivity= 52.4%
Specificity= 85.7%

Figure 12

**VirB 10 (*Anaplasma phagocytophilum* HZ)**

Figure 13

VirB 10 Protein Fragment 1

Nucleotide Sequence (SEQ ID No. 12)

```
  1 ATGGCTGACG AAATAAGGGG TTCTAGCAGC GGGGAGAACA TTGAGGATAA
 51 TGTTAATGTA GTAGGTGTAG CAAAGAGTAA GAAGCTCTTT GTTATCATAG
101 TGGTGCTGAT TGCTACTGGA CTTATGTACT ATTTTTTCTT CTTCAATAAG
151 GAGTCTTCGG ATAATGAGGA AGATACTCAG ATTCCTCGTG TTATCGAAGA
201 GAAGGAAGTA GAAAAATTGA GGAAGGATGC GGGAAGGCCG GCTCAGGAGA
251 CTGCTCCTAG AATCTTGACG CCA
```

Deduced Amino Acid Sequence (SEQ ID No. 13)

```
MADEIRGSSSGENIEDNVNVVGVAKSKKLFVIIVVLIATGLMYYFFFNK 50
ESSDNEEDTQIPRVIEEKEVEKLRKDAGRPAQETAPRILTP*
```

Figure 14

VirB 10 Protein Fragment 2

Nucleotide Sequence (SEQ ID No. 14)

```
  1 CAGATTCCTC GTGTTATCGA AGAGAAGGAA GTAGAAAAAT TGAGGAAGGA
 51 TGCGGGAAGG CCGGCTCAGG AGACTGCTCC TAGAATCTTG ACGCCACCAC
101 CGAGGTTGCC TGAGTTGCCG CCGCTTGTAA TGCCTACTGT ACCTGATATT
151 CCTGTGGTAA CAAAATTGCT TAAGCCGCCT GTAGAGGAGG AGTTTGTTGA
201 AGAGTATAAC GTTCAAGAGG TTCCTTCACC AATGGGTAAT ATTGCTCCTC
251 CTGAACGCGA GGAGATATCT TTACCTTTGC CGTATAAGAC GATAACAACT
301 GAGCAGCCGT CGTTTCTGGG GTATGATAAA GAAAAAGAG GAGCCCCTAT
351 GATCGCATTT GGTGGCGGTG GTGGCGAAGC TGCTGGTAGT GAATCCGGTG
401 ATGGTTCTGT TGGCGGGAAG GAA
```

Deduced Amino Acid Sequence (SEQ ID No. 15)

```
MPTVPDIPVVTKLLKPPVEEEFVEEYNVQEVPSPMGNIAPPEREEISLPL 50
PYKTITTEQPSFLGYDKEKRGAPMIAFGGGGEAAGSESGDGSVGGKE*
```

Figure 15

VirB 10 Protein Fragment 3

Nucleotide Sequence (SEQ ID No. 16)

```
  1 GAAGATGCTC GGTTTACTGC GTGGCAAGGG TTAGAGGGTA CTCAATCTCC
 51 TAGTGTTAGA GCGACAAGAG TGGGGGATAC GAGATATATA ATACTGCAAG
101 GTCACATGAT TGATGCTGTT TTAGAGACAG CAATAAACTC GGATATTTCA
151 GGGGTGCTCA GGGCTGTGGT ATCCAGAGAT GTATATGCTT CTTCTGGAGA
201 TGCGGTTGTA ATACCGAAGG GGTCTAGGCT TATTGGTAGT TATTTCTTTG
251 ATTCTGCTGG TAACAATGTA AGGGTTGATG TTAATTGGTC CAGGGTCATT
301 TTACCTCATG GCGTTGATAT ACAGATAGCG TCTAGTGGAA CTGATGAACT
351 AGGAAGAAAT GGTATTTCTG GTGTTGTAGA TAATAAAGTG GGC
```

Deduced Amino Acid Sequence (SEQ ID No. 17)

```
MIDAVLETAINSDISGVLRAVVSRDVYASSGDAVVIPKGSRLIGSYFFDS 50
AGNNVRVDVNWSRVILPHGVDIQIASSGTDELGRNGISGVVDNKVG*
```

Figure 16

VirB 10 Protein Fragment 4

Nucleotide Sequence (SEQ ID No. 18)

```
  1 TTACCTCATG GCGTTGATAT ACAGATAGCG TCTAGTGGAA CTGATGAACT
 51 AGGAAGAAAT GGTATTTCTG GTGTTGTAGA TAATAAAGTG GGCTCCATAT
101 TGACCTCTAC TATCTTTTTG GCGGGTATAT CTTTGGGGAC AGCTTATGTG
151 ACCGAGCAGA TACCGTCGTT GCGGACTGAG ACTGTTAAGG TTGAGACTCC
201 TGCGGATGGT AAAGACGGGA AGAAAACTAC TTCATCATCT CTTTCAACAA
251 AGATAGTTTC TGATGCTATT AAGGATTTCT CTGACTCTAT GAAAGAGATT
301 GTGAATAAGT ATTCTAATAG GACTCCGACT GTCTATGTAG ATCAGGGTAC
351 TGTGATGAAG GTATTTGTGA ATCAGGACGT AGTATTTCCT CGTGATGCGG
401 TGAGGTAG
```

Deduced Amino Acid Sequence (SEQ ID No. 19)

MKEIVNKYSNRTPTVYVDQGTVMKVFVNQDVVFPRDAVR*

Figure 17

VirB 10 Fragment 5

Nucleotide Sequence (SEQ ID No. 20)

```
  1 CCGCTTGTAA TGCCTACTGT ACCTGATATT CCTGTGGTAA CAAAATTGCT
 51 TAAGCCGCCT GTAGAGGAGG AGTTTGTTGA AGAGTATAAC GTTCAAGAGG
101 TTCCTTCACC AATGGGTAAT ATTGCTCCTC CTGAACGCGA GGAGATATCT
151 TTACCTTTGC CGTATAAGAC GATAACAACT GAGCAGCCGT CGTTTCTGGG
201 GTATGATAAA GAAAAAGAG GAGCCCCTAT GATCGCATTT GGTGGCGGTG
251 GTGGCGAAGC TGCTGGTAGT GAATCCGGTG ATGGTTCTGT TGGCGGGAAG
301 GAAGATGCTC GGTTTACTGC GTGGCAAGGG TTAGAGGGTA CTCAATCTCC
351 TAGTGTTAGA GCGACAAGAG TGGGGGATAC GAGATATATA ATACTGCAAG
401 GTCACATGAT TGATGCTGTT TTAGAGACAG CAATAAACTC GGATATTTCA
451 GGGGTGCTCA GGGCTGTGGT ATCCAGAGAT GTATATGCTT CTTCTGGAGA
501 TGCGGTTGTA ATACCGAAGG GGTCTAGGCT TATTGGTAGT TATTTCTTTG
551 ATTCTGCTGG TAACAATGTA AGGGTTGATG TTAATTGGTC CAGGGTCATT
601 TTA
```

Deduced Amino Acid Sequence (SEQ ID No. 21)

```
MPTVPDIPVVTKLLKPPVEEEFVEEYNVQEVPSPMGNIAPPEREEISLPL 50
PYKTITTEQPSFLGYDKEKRGAPMIAFGGGGEAAGSESGDGSVGGKEDA 100
RFTAWQGLEGTQSPSVRATRVGDTRYIILQGHMIDAVLETAINSDISGVL 150
RAVVSRDVYASSGDAVVIPKGSRLIGSYFFDSAGNNVRVDVNWSRVIL*
```

Colony PCR of virB10 Fragments in NovaBlue *E. coli*

Colony PCR of virB10 Fragment 4 in NovaBlue *E. coli*

Purification of virB10 Fragments 3 and 4 from inclusion body pellet

Nickel Column Purification of virB10 Fragment-5 virB10 Fragments 1 and 2 (combined) IgM ELISA

Sensitivity: 81.0%
Specificity: 85.7%

Figure 37
IgG ELISA Analysis of virB10 Fragments 3 and 4
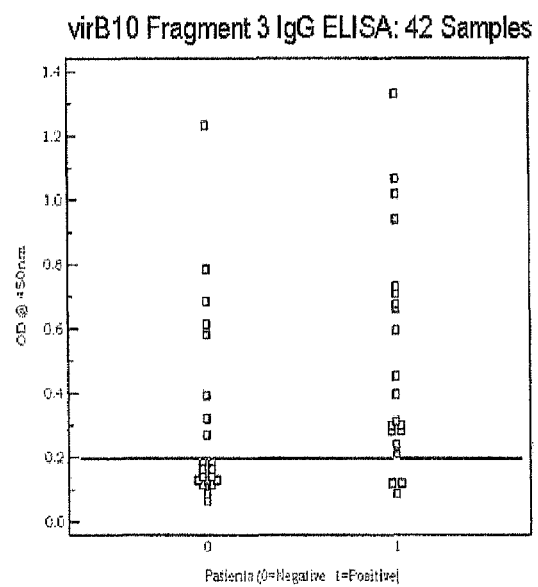
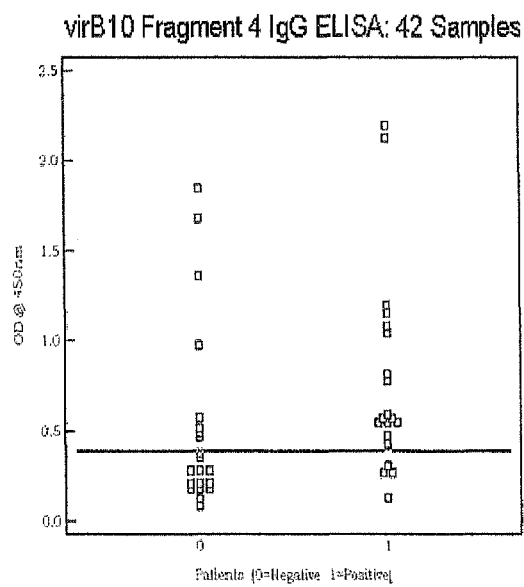
Sensitivity: 85.7%
Specificity: 61.9%
Sensitivity: 81.0%
Specificity: 61.9%

IgG ELISA Analysis of virB10 Fragment 5

Sensitivity: 76.2%
Specificity: 66.7%

SEQUENCE LISTING

```
<160> NUMBER OF SEQ ID NOS: 31

<210> SEQ ID NO 1
<211> LENGTH: 35
<212> TYPE: DNA
<213> ORGANISM: Anaplasma Phagocytophilum
<220> FEATURE:
<223> OTHER INFORMATION: Primer

<400> SEQUENCE: 1
gacgacgaca agatggctga cgaaataagg ggttc                                35

<210> SEQ ID NO 2
<211> LENGTH: 33
<212> TYPE: DNA
<213> ORGANISM: Anaplasma Phagocytophilum
<220> FEATURE:
<223> OTHER INFORMATION: Primer

<400> SEQUENCE: 2
gaggagaagc ccggtctacc tcaccgcatc acg                                  33

<210> SEQ ID NO 3
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 3
gacgacgaca agatggtgca gttttctttg cc                                   32

<210> SEQ ID NO 4
<211> LENGTH: 37
<212> TYPE: DNA
<213> ORGANISM: Anaplasma Phagocytophilum
<220> FEATURE:
<223> OTHER INFORMATION: Primer

<400> SEQUENCE: 4
gaggagaagc ccggtctaga gctccaatcc ttttatc                              37

<210> SEQ ID NO 5
<211> LENGTH: 34
<212> TYPE: DNA
<213> ORGANISM: Anaplasma Phagocytophilum
<220> FEATURE:
<223> OTHER INFORMATION: Primer
```

-continued

```
<400> SEQUENCE: 5
gacgacgaca agatgctaag gctcatggtg atgg                                34

<210> SEQ ID NO 6
<211> LENGTH: 36
<212> TYPE: DNA
<213> ORGANISM: Anaplasma Phagocytophilum
<220> FEATURE:
<223> OTHER INFORMATION: Primer

<400> SEQUENCE: 6
gaggagaagc ccggttcaaa aacgtattgt gcgacg                              36

<210> SEQ ID NO 7
<211> LENGTH: 434
<212> TYPE: PRT
<213> ORGANISM: Anaplasma Phagocytophilum

<400> SEQUENCE: 7
```

Met Ala Asp Glu Ile Arg Gly Ser Ser Gly Glu Asn Ile Glu Asp
1               5                   10                  15

Asn Val Asn Val Val Gly Val Ala Lys Ser Lys Lys Leu Phe Val Ile
            20                  25                  30

Ile Val Val Leu Ile Ala Thr Gly Leu Met Tyr Tyr Phe Phe Phe
        35                  40                  45

Asn Lys Glu Ser Ser Asp Asn Glu Glu Asp Thr Gln Ile Pro Arg Val
    50                  55                  60

Ile Glu Glu Lys Glu Val Glu Lys Leu Arg Lys Asp Ala Gly Arg Pro
65                  70                  75                  80

Ala Gln Glu Thr Ala Pro Arg Ile Leu Thr Pro Pro Arg Leu Pro
                85                  90                  95

Glu Leu Pro Pro Leu Val Met Pro Thr Val Pro Asp Ile Pro Val Val
            100                 105                 110

Thr Lys Leu Leu Lys Pro Pro Val Glu Glu Phe Val Glu Glu Tyr
        115                 120                 125

Asn Val Gln Glu Val Pro Ser Pro Met Gly Asn Ile Ala Pro Pro Glu
    130                 135                 140

Arg Glu Glu Ile Ser Leu Pro Leu Pro Tyr Lys Thr Ile Thr Thr Glu
145                 150                 155                 160

Gln Pro Ser Phe Leu Gly Tyr Asp Lys Glu Lys Arg Gly Ala Pro Met
                165                 170                 175

Ile Ala Phe Gly Gly Gly Gly Glu Ala Ala Gly Ser Glu Ser Gly
            180                 185                 190

Asp Gly Ser Val Gly Gly Lys Glu Asp Ala Arg Phe Thr Ala Trp Gln
        195                 200                 205

Gly Leu Glu Gly Thr Gln Ser Pro Ser Val Arg Ala Thr Arg Val Gly
    210                 215                 220

Asp Thr Arg Tyr Ile Ile Leu Gln Gly His Met Ile Asp Ala Val Leu
225                 230                 235                 240

Glu Thr Ala Ile Asn Ser Asp Ile Ser Gly Val Leu Arg Ala Val Val
                245                 250                 255

Ser Arg Asp Val Tyr Ala Ser Ser Gly Asp Ala Val Val Ile Pro Lys
            260                 265                 270

Gly Ser Arg Leu Ile Gly Ser Tyr Phe Phe Asp Ser Ala Gly Asn Asn
        275                 280                 285

Val Arg Val Asp Val Asn Trp Ser Arg Val Ile Leu Pro His Gly Val
    290                 295                 300

```
Asp Ile Gln Ile Ala Ser Ser Gly Thr Asp Glu Leu Gly Arg Asn Gly
305                 310                 315                 320

Ile Ser Gly Val Val Asp Asn Lys Val Gly Ser Ile Leu Thr Ser Thr
            325                 330                 335

Ile Phe Leu Ala Gly Ile Ser Leu Gly Thr Ala Tyr Val Thr Glu Gln
            340                 345                 350

Ile Pro Ser Leu Arg Thr Glu Thr Val Lys Val Glu Thr Pro Ala Asp
            355                 360                 365

Gly Lys Asp Gly Lys Lys Thr Thr Ser Ser Ser Leu Ser Thr Lys Ile
370                 375                 380

Val Ser Asp Ala Ile Lys Asp Phe Ser Asp Ser Met Lys Glu Ile Val
385                 390                 395                 400

Asn Lys Tyr Ser Asn Arg Thr Pro Thr Val Tyr Val Asp Gln Gly Thr
            405                 410                 415

Val Met Lys Val Phe Val Asn Gln Asp Val Val Phe Pro Arg Asp Ala
            420                 425                 430

Val Arg

<210> SEQ ID NO 8
<211> LENGTH: 262
<212> TYPE: PRT
<213> ORGANISM: Anaplasma Phagocytophilum

<400> SEQUENCE: 8

Met Val Gln Phe Ser Leu Pro Lys Asn Ser Lys Ile Asn Pro Asn Gly
1               5                   10                  15

Lys Val Tyr Asn Ala Thr Glu Gly Ala Lys Arg Thr Gly Cys Phe Lys
            20                  25                  30

Ile Tyr Arg Trp Ser Pro Asp Asp Gly Glu Asn Pro Arg Ile Asp Thr
        35                  40                  45

Tyr Tyr Ile Asp Leu Asp Lys Cys Gly Gln Met Val Leu Asp Ala Leu
    50                  55                  60

Ile Lys Val Lys Asn Glu Tyr Asp Ser Thr Leu Thr Phe Arg Arg Ser
65                  70                  75                  80

Cys Arg Glu Gly Ile Cys Gly Ser Cys Ala Met Asn Ile Asp Gly Thr
            85                  90                  95

Asn Thr Leu Ala Cys Thr Lys Tyr Ile Ser Asp Ile Lys Gly Asp Val
            100                 105                 110

Lys Ile Phe Pro Leu Pro His Met Asp Val Ile Lys Asp Leu Val Pro
        115                 120                 125

Asp Leu Ser Asn Phe Tyr Lys Gln Tyr Lys Ser Ile Ser Pro Trp Leu
    130                 135                 140

Lys Ser Asp Gly Ala Arg Ser Asp Arg Glu Glu His Leu Gln Ser Ile
145                 150                 155                 160

Glu Asp Arg Ser Lys Leu Asp Lys Val Tyr Asp Cys Ile Leu Cys Ala
            165                 170                 175

Cys Cys Ser Thr Ser Cys Pro Ser Tyr Trp Trp Asn Pro Asp Lys Tyr
            180                 185                 190

Leu Gly Pro Ala Ala Leu Leu Gln Val Tyr Arg Trp Leu Val Asp Ser
        195                 200                 205

Arg Asp Thr Ala Thr Glu Glu Arg Leu Ala Phe Leu Glu Asp Ala Phe
    210                 215                 220

Lys Leu Tyr Arg Cys His Thr Ile Met Asn Cys Thr Lys Thr Cys Pro
225                 230                 235                 240
```

-continued

```
Lys Asp Leu Asn Pro Ala Lys Ala Ile Ala Lys Ile Lys Gln Met Met
                245                 250                 255

Ile Lys Gly Leu Glu Leu
            260

<210> SEQ ID NO 9
<211> LENGTH: 335
<212> TYPE: PRT
<213> ORGANISM: Anaplasma Phagocytophilum

<400> SEQUENCE: 9

Met Leu Arg Leu Met Val Met Val Val Leu Gln Gly Ser Gly Arg Ala
1               5                   10                  15

Gly Tyr Phe Tyr Val Gly Leu Asp Tyr Ser Pro Ala Phe Ser Lys Ile
                20                  25                  30

Arg Asp Phe Ser Ile Arg Glu Ser Asn Gly Glu Thr Lys Ala Val Tyr
            35                  40                  45

Pro Tyr Leu Lys Asp Gly Lys Ser Val Lys Leu Glu Ser Asn Lys Phe
        50                  55                  60

Asp Trp Asn Thr Pro Asp Pro Arg Ile Gly Phe Lys Asp Asn Met Leu
65                  70                  75                  80

Val Ala Met Glu Gly Ser Val Gly Tyr Gly Ile Gly Gly Ala Arg Val
                85                  90                  95

Glu Leu Glu Ile Gly Tyr Glu Arg Phe Lys Thr Lys Gly Ile Arg Asp
                100                 105                 110

Ser Gly Ser Lys Glu Asp Glu Ala Asp Thr Val Tyr Leu Leu Ala Lys
            115                 120                 125

Glu Leu Ala Tyr Asp Val Val Thr Gly Gln Thr Asp Asn Leu Ala Ala
        130                 135                 140

Ala Leu Ala Lys Thr Ser Gly Lys Asp Phe Val Gln Phe Ala Lys Ala
145                 150                 155                 160

Val Val Val Ser His Pro Gly Ile Asp Lys Lys Val Cys Ala Thr Lys
                165                 170                 175

Ala Gln Ser Ser Gly Lys Tyr Gly Lys Tyr Ala Asp Lys Thr Gly Thr
                180                 185                 190

Lys Ser Ser Asp Asn Asn Thr Ser Leu Cys Ser Asp Asp Gly Gly Ser
            195                 200                 205

His Ser Gly Ser Ser Asn Ala Glu Val Phe Glu His Phe Ile Lys
        210                 215                 220

Lys Thr Leu Leu Glu Asn Gly Ser Lys Asn Trp Pro Thr Ser Thr Lys
225                 230                 235                 240

Asn Asp Gly Ala Pro Ser Asp Asn Lys Asn Asp Asn Ala Asp Ala Val
                245                 250                 255

Ala Lys Asp Leu Thr Lys Leu Thr Ser Glu Glu Lys Thr Ile Val Ala
                260                 265                 270

Gly Leu Leu Ala Lys Thr Ile Glu Gly Gly Glu Val Val Glu Ile Arg
            275                 280                 285

Ala Val Ser Ser Thr Ser Val Met Val Asn Ala Cys Tyr Asp Leu Leu
        290                 295                 300

Ser Glu Gly Leu Gly Val Val Pro Tyr Ala Cys Val Gly Leu Gly Gly
305                 310                 315                 320

Asn Phe Val Gly Val Val Asp Gly Ser Arg Arg Thr Ile Arg Phe
                325                 330                 335
```

<210> SEQ ID NO 10
<211> LENGTH: 1305
<212> TYPE: DNA
<213> ORGANISM: Anaplasma Phagocytophilum

<400> SEQUENCE: 10

| | | | | | |
|---|---|---|---|---|---|
| atggctgacg | aaataagggg | ttctagcagc | ggggagaaca | ttgaggataa | tgttaatgta | 60 |
| gtaggtgtag | caaagagtaa | gaagctcttt | gttatcatag | tggtgctgat | tgctactgga | 120 |
| cttatgtact | attttttctt | cttcaataag | gagtcttcgg | ataatgagga | agatactcag | 180 |
| attcctcgtg | ttatcgaaga | gaaggaagta | gaaaaattga | ggaaggatgc | gggaaggccg | 240 |
| gctcaggaga | ctgctcctag | aatcttgacg | ccaccaccga | ggttgcctga | gttgccgccg | 300 |
| cttgtaatgc | ctactgtacc | tgatattcct | gtggtaacaa | aattgcttaa | gccgcctgta | 360 |
| gaggaggagt | ttgttgaaga | gtaaacgtt | caagaggttc | cttcaccaat | gggtaatatt | 420 |
| gctcctcctg | aacgcgagga | gatatcttta | cctttgccgt | ataagacgat | aacaactgag | 480 |
| cagccgtcgt | ttctgggta | tgataaagaa | aaaagaggag | cccctatgat | cgcatttggt | 540 |
| ggcggtggtg | gcgaagctgc | tggtagtgaa | tccggtgatg | gttctgttgg | cgggaaggaa | 600 |
| gatgctcggt | tactgcgtg | gcaagggtta | gagggtactc | aatctcctag | tgttagagcg | 660 |
| acaagagtgg | gggatacgag | atatataata | ctgcaaggtc | acatgattga | tgctgtttta | 720 |
| gagacagcaa | taaactcgga | tatttcaggg | gtgctcaggg | ctgtggtatc | cagagatgta | 780 |
| tatgcttctt | ctggagatgc | ggttgtaata | ccgaaggggt | ctaggcttat | tggtagttat | 840 |
| ttctttgatt | ctgctggtaa | caatgtaagg | gttgatgtta | attggtccag | ggtcatttta | 900 |
| cctcatggcg | ttgatataca | gatagcgtct | agtggaactg | atgaactagg | aagaaatggt | 960 |
| atttctggtg | ttgtagataa | taagtgggc | tccatattga | cctctactat | cttttttggcg | 1020 |
| ggtatatctt | tggggacagc | ttatgtgacc | gagcagatac | cgtcgttgcg | gactgagact | 1080 |
| gttaaggttg | agactcctgc | ggatggtaaa | gacgggaaga | aaactacttc | atcatctctt | 1140 |
| tcaacaaaga | tagtttctga | tgctattaag | gatttctctg | actctatgaa | agagattgtg | 1200 |
| aataagtatt | ctaataggac | tccgactgtc | tatgtagatc | agggtactgt | gatgaaggta | 1260 |
| tttgtgaatc | aggacgtagt | atttcctcgt | gatgcggtga | ggtag | | 1305 |

<210> SEQ ID NO 11
<211> LENGTH: 434
<212> TYPE: PRT
<213> ORGANISM: Anaplasma Phagocytophilum

<400> SEQUENCE: 11

Met Ala Asp Glu Ile Arg Gly Ser Ser Gly Glu Asn Ile Glu Asp
1               5                   10                  15

Asn Val Asn Val Val Gly Val Ala Lys Ser Lys Lys Leu Phe Val Ile
                20                  25                  30

Ile Val Val Leu Ile Ala Thr Gly Leu Met Tyr Tyr Phe Phe Phe Phe
                35                  40                  45

Asn Lys Glu Ser Ser Asp Asn Glu Glu Asp Thr Gln Ile Pro Arg Val
            50                  55                  60

Ile Glu Glu Lys Glu Val Glu Lys Leu Arg Lys Asp Ala Gly Arg Pro
65                  70                  75                  80

Ala Gln Glu Thr Ala Pro Arg Ile Leu Thr Pro Pro Arg Leu Pro
                85                  90                  95

Glu Leu Pro Pro Leu Val Met Pro Thr Val Pro Asp Ile Pro Val Val
                100                 105                 110

```
Thr Lys Leu Leu Lys Pro Pro Val Glu Glu Phe Val Glu Glu Tyr
        115                 120                 125
Asn Val Gln Glu Val Pro Ser Pro Met Gly Asn Ile Ala Pro Pro Glu
    130                 135                 140
Arg Glu Glu Ile Ser Leu Pro Leu Pro Tyr Lys Thr Ile Thr Thr Glu
145                 150                 155                 160
Gln Pro Ser Phe Leu Gly Tyr Asp Lys Glu Lys Arg Gly Ala Pro Met
                165                 170                 175
Ile Ala Phe Gly Gly Gly Gly Glu Ala Ala Gly Ser Glu Ser Gly
                180                 185                 190
Asp Gly Ser Val Gly Gly Lys Glu Asp Ala Arg Phe Thr Ala Trp Gln
            195                 200                 205
Gly Leu Glu Gly Thr Gln Ser Pro Ser Val Arg Ala Thr Arg Val Gly
        210                 215                 220
Asp Thr Arg Tyr Ile Ile Leu Gln Gly His Met Ile Asp Ala Val Leu
225                 230                 235                 240
Glu Thr Ala Ile Asn Ser Asp Ile Ser Gly Val Leu Arg Ala Val Val
                245                 250                 255
Ser Arg Asp Val Tyr Ala Ser Ser Gly Asp Ala Val Ile Pro Lys
                260                 265                 270
Gly Ser Arg Leu Ile Gly Ser Tyr Phe Phe Asp Ser Ala Gly Asn Asn
            275                 280                 285
Val Arg Val Asp Val Asn Trp Ser Arg Val Ile Leu Pro His Gly Val
        290                 295                 300
Asp Ile Gln Ile Ala Ser Ser Gly Thr Asp Leu Gly Arg Asn Gly
305                 310                 315                 320
Ile Ser Gly Val Val Asp Asn Lys Val Gly Ser Ile Leu Thr Ser Thr
                325                 330                 335
Ile Phe Leu Ala Gly Ile Ser Leu Gly Thr Ala Tyr Val Thr Glu Gln
            340                 345                 350
Ile Pro Ser Leu Arg Thr Glu Thr Val Lys Val Glu Thr Pro Ala Asp
        355                 360                 365
Gly Lys Asp Gly Lys Lys Thr Thr Ser Ser Ser Leu Ser Thr Lys Ile
370                 375                 380
Val Ser Asp Ala Ile Lys Asp Phe Ser Asp Ser Met Lys Glu Ile Val
385                 390                 395                 400
Asn Lys Tyr Ser Asn Arg Thr Pro Thr Val Tyr Val Asp Gln Gly Thr
                405                 410                 415
Val Met Lys Val Phe Val Asn Gln Asp Val Val Phe Pro Arg Asp Ala
            420                 425                 430
Val Arg

<210> SEQ ID NO 12
<211> LENGTH: 273
<212> TYPE: DNA
<213> ORGANISM: Anaplasma Phagocytophilum

<400> SEQUENCE: 12
atggctgacg aaataagggg ttctagcagc ggggagaaca ttgaggataa tgttaatgta      60
gtaggtgtag caaagagtaa gaagctcttt gttatcatag tggtgctgat tgctactgga     120
cttatgtact ttttttcttt cttcaataag gagtcttcgg ataatgagga agatactcag     180
attcctcgtg ttatcgaaga gaaggaagta gaaaaattga ggaaggatgc gggaaggccg     240
gctcaggaga ctgctcctag aatcttgacg cca                                  273
```

```
<210> SEQ ID NO 13
<211> LENGTH: 91
<212> TYPE: PRT
<213> ORGANISM: Anaplasma Phagocytophilum

<400> SEQUENCE: 13
```

Met Ala Asp Glu Ile Arg Gly Ser Ser Gly Glu Asn Ile Glu Asp
1               5                   10                  15

Asn Val Asn Val Val Gly Val Ala Lys Ser Lys Lys Leu Phe Val Ile
            20                  25                  30

Ile Val Val Leu Ile Ala Thr Gly Leu Met Tyr Tyr Phe Phe Phe
        35                  40                  45

Asn Lys Glu Ser Ser Asp Asn Glu Glu Asp Thr Gln Ile Pro Arg Val
50                  55                  60

Ile Glu Glu Lys Glu Val Glu Lys Leu Arg Lys Asp Ala Gly Arg Pro
65                  70                  75                  80

Ala Gln Glu Thr Ala Pro Arg Ile Leu Thr Pro
            85                  90

```
<210> SEQ ID NO 14
<211> LENGTH: 423
<212> TYPE: DNA
<213> ORGANISM: Anaplasma Phagocytophilum
<400> SEQUENCE: 14
cagattcctc gtgttatcga agagaaggaa gtagaaaaat tgaggaagga tgcgggaagg      60
ccggctcagg agactgctcc tagaatcttg acgccaccac cgaggttgcc tgagttgccg     120
ccgcttgtaa tgcctactgt acctgatatt cctgtggtaa caaaattgct taagccgcct     180
gtagaggagg agtttgttga agagtataac gttcaagagg ttccttcacc aatgggtaat     240
attgctcctc ctgaacgcga ggagatatct ttacctttgc cgtataagac gataacaact     300
gagcagccgt cgtttctggg gtatgataaa gaaaaaagag gagcccctat gatcgcattt     360
ggtggcggtg gtggcgaagc tgctggtagt gaatccggtg atggttctgt tgcgggaag      420
gaa                                                                   423

<210> SEQ ID NO 15
<211> LENGTH: 98
<212> TYPE: PRT
<213> ORGANISM: Anaplasma Phagocytophilum

<400> SEQUENCE: 15
```

Met Pro Thr Val Pro Asp Ile Pro Val Val Thr Lys Leu Leu Lys Pro
1               5                   10                  15

Pro Val Glu Glu Glu Phe Val Glu Glu Tyr Asn Val Gln Glu Val Pro
            20                  25                  30

Ser Pro Met Gly Asn Ile Ala Pro Pro Glu Arg Glu Glu Ile Ser Leu
        35                  40                  45

Pro Leu Pro Tyr Lys Thr Ile Thr Thr Glu Gln Pro Ser Phe Leu Gly
50                  55                  60

Tyr Asp Lys Glu Lys Arg Gly Ala Pro Met Ile Ala Phe Gly Gly Gly
65                  70                  75                  80

Gly Gly Glu Ala Ala Gly Ser Glu Ser Gly Asp Gly Ser Val Gly Gly
            85                  90                  95

Lys Glu

<210> SEQ ID NO 16
<211> LENGTH: 393
<212> TYPE: DNA
<213> ORGANISM: Anaplasma Phagocytophilum

<400> SEQUENCE: 16

```
gaagatgctc ggtttactgc gtggcaaggg ttagagggta ctcaatctcc tagtgttaga      60
gcgacaagag tgggggatac gagatatata atactgcaag gtcacatgat tgatgctgtt     120
ttagagacag caataaactc ggatatttca ggggtgctca gggctgtggt atccagagat     180
gtatatgctt cttctggaga tgcggttgta ataccgaagg gtctaggct tattggtagt      240 tatttctttg attctgctgg taacaatgta agggttgatg ttaattggtc cagggtcatt     300
ttacctcatg gcgttgatat acagatagcg tctagtggaa ctgatgaact aggaagaaat     360
ggtatttctg gtgttgtaga taataaagtg ggc                                  393
```

<210> SEQ ID NO 17
<211> LENGTH: 96
<212> TYPE: PRT
<213> ORGANISM: Anaplasma Phagocytophilum

<400> SEQUENCE: 17

Met Ile Asp Ala Val Leu Glu Thr Ala Ile Asn Ser Asp Ile Ser Gly
1               5                   10                  15

Val Leu Arg Ala Val Val Ser Arg Asp Val Tyr Ala Ser Ser Gly Asp
            20                  25                  30

Ala Val Val Ile Pro Lys Gly Ser Arg Leu Ile Gly Ser Tyr Phe Phe
        35                  40                  45

Asp Ser Ala Gly Asn Asn Val Arg Val Asp Val Asn Trp Ser Arg Val
    50                  55                  60

Ile Leu Pro His Gly Val Asp Ile Gln Ile Ala Ser Ser Gly Thr Asp
65                  70                  75                  80

Glu Leu Gly Arg Asn Gly Ile Ser Gly Val Val Asp Asn Lys Val Gly
                85                  90                  95

<210> SEQ ID NO 18
<211> LENGTH: 408
<212> TYPE: DNA
<213> ORGANISM: Anaplasma Phagocytophilum

<400> SEQUENCE: 18

```
ttacctcatg gcgttgatat acagatagcg tctagtggaa ctgatgaact aggaagaaat      60
ggtatttctg gtgttgtaga taataaagtg ggctccatat tgacctctac tatcttttg     120 gcgggtatat ctttggggac agcttatgtg accgagcaga taccgtcgtt gcggactgag     180
actgttaagg ttgagactcc tgcggatggt aaagacggga agaaaactac ttcatcatct     240
ctttcaacaa agatagtttc tgatgctatt aaggatttct ctgactctat gaaagagatt     300
gtgaataagt attctaatag gactccgact gtctatgtag atcagggtac tgtgatgaag     360
gtatttgtga atcaggacgt agtatttcct cgtgatgcgg tgaggtag                  408
```

<210> SEQ ID NO 19
<211> LENGTH: 39
<212> TYPE: PRT
<213> ORGANISM: Anaplasma Phagocytophilum

<400> SEQUENCE: 19

Met Lys Glu Ile Val Asn Lys Tyr Ser Asn Arg Thr Pro Thr Val Tyr
1               5                   10                  15

Val Asp Gln Gly Thr Val Met Lys Val Phe Val Asn Gln Asp Val Val
            20                  25                  30

Phe Pro Arg Asp Ala Val Arg
        35

<210> SEQ ID NO 20
<211> LENGTH: 603
<212> TYPE: DNA
<213> ORGANISM: Anaplasma Phagocytophilum

<400> SEQUENCE: 20
ccgcttgtaa tgcctactgt acctgatatt cctgtggtaa caaaattgct taagccgcct      60
gtagaggagg agtttgttga agagtataac gttcaagagg ttccttcacc aatgggtaat     120
attgctcctc ctgaacgcga ggagatatct ttacctttgc cgtataagac gataacaact     180
gagcagccgt cgtttctggg gtatgataaa gaaaaagag gagcccctat gatcgcattt      240
ggtggcggtg gtggcgaagc tgctggtagt gaatccggtg atggttctgt ggcgggaag      300
gaagatgctc ggtttactgc gtggcaaggg ttagagggta ctcaatctcc tagtgttaga     360
gcgacaagag tggggatac gagatatata atactgcaag gtcacatgat tgatgctgtt     420
ttagagacag caataaactc ggatatttca ggggtgctca gggctgtggt atccagagat     480
gtatatgctt cttctggaga tgcggttgta ataccgaagg ggtctaggct tattggtagt     540
tatttctttg attctgctgg taacaatgta agggttgatg ttaattggtc cagggtcatt     600
tta                                                                   603

<210> SEQ ID NO 21
<211> LENGTH: 198
<212> TYPE: PRT
<213> ORGANISM: Anaplasma Phagocytophilum

<400> SEQUENCE: 21

Met Pro Thr Val Pro Asp Ile Pro Val Val Thr Lys Leu Leu Lys Pro
1               5                   10                  15

Pro Val Glu Glu Glu Phe Val Glu Glu Tyr Asn Val Gln Glu Val Pro
            20                  25                  30

Ser Pro Met Gly Asn Ile Ala Pro Pro Glu Arg Glu Glu Ile Ser Leu
        35                  40                  45

Pro Leu Pro Tyr Lys Thr Ile Thr Thr Glu Gln Pro Ser Phe Leu Gly
    50                  55                  60

Tyr Asp Lys Glu Lys Arg Gly Ala Pro Met Ile Ala Phe Gly Gly Gly
65                  70                  75                  80

Gly Gly Glu Ala Ala Gly Ser Glu Ser Gly Asp Gly Ser Val Gly Gly
                85                  90                  95

Lys Glu Asp Ala Arg Phe Thr Ala Trp Gln Gly Leu Glu Gly Thr Gln
            100                 105                 110

Ser Pro Ser Val Arg Ala Thr Arg Val Gly Asp Thr Arg Tyr Ile Ile
        115                 120                 125

Leu Gln Gly His Met Ile Asp Ala Val Leu Glu Thr Ala Ile Asn Ser
    130                 135                 140

Asp Ile Ser Gly Val Leu Arg Ala Val Val Ser Arg Asp Val Tyr Ala
145                 150                 155                 160

-continued

Ser Ser Gly Asp Ala Val Val Ile Pro Lys Gly Ser Arg Leu Ile Gly
                165                 170                 175

Ser Tyr Phe Phe Asp Ser Ala Gly Asn Asn Val Arg Val Asp Val Asn
            180                 185                 190

Trp Ser Arg Val Ile Leu
        195

<210> SEQ ID NO 22
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 22
gacgacgaca agatgatggc tgacgaaata ag                                32

<210> SEQ ID NO 23
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 23
gaggagaagc ccggttatgg cgtcaagatt ct                                32

<210> SEQ ID NO 24
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 24
gacgacgaca agatgcagat tcctcgtgtt at                                32

<210> SEQ ID NO 25
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 25
gaggagaagc ccggttattc cttcccgcca ac                                32

<210> SEQ ID NO 26
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 26
gacgacgaca agatggaaga tgctcggttt ac                                32

<210> SEQ ID NO 27
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 27
gaggagaagc ccggttagcc cactttatta tc                                32

-continued

```
<210> SEQ ID NO 28
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 28
gacgacgaca agatgttacc tcatggcgtt ga                              32

<210> SEQ ID NO 29
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 29
gaggagaagc ccggttacta cctcaccgca tc                              32

<210> SEQ ID NO 30
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 30
gacgacgaca agatgccgct tgtaatgcct ac                              32

<210> SEQ ID NO 31
<211> LENGTH: 32
<212> TYPE: DNA
<213> ORGANISM: Anaplasma Phagocytophilum
<220> FEATURE:
<223> OTHER INFORMATION: Primer

<400> SEQUENCE: 31
gaggagaagc ccggttataa aatgaccctg ga                              32
```

PROTEIN FRAGMENTS OF VIRB10 AND SERO-DETECTION OF *ANAPLASMA PHAGOCYTOPHILUM*

CROSS-REFERENCE TO RELATED APPLICATIONS

This application is a division of application Ser. No. 12/658,506, filed Feb. 9, 2010, which claims the benefit under 35 U.S.C.§119(e), of U.S. Provisional Application No. 61/208,761, filed Feb. 27, 2009, the contents of which are incorporated by reference herein in their entirety.

FIELD OF THE INVENTION

The present invention generally relates to the field of diagnostic assays for the detection of infectious agents in an animal, including humans. Particular embodiments disclosed herein encompass protein fragments of virB10 (a Type IV Secretion Protein System) (TIVSS) that are useful in the sero-detection of *Anaplasma phagocytophilum*.

BACKGROUND OF THE INVENTION

*Anaplasma phagocytophilum* is a tick-borne pathogen responsible for granulocytic anaplasmosis in humans (Bakken J. S., et al.: Human granulocytic ehrlichiosis in the upper Midwest United States. A new species emerging? *JAMA* 272: 212-218, 1994). There has been a steady rise in cases of *anaplasma* infections, alone or through co-infection with other tick-borne pathogens (Varde S., et al.: Prevalence of tick-borne pathogens in *Ixodes scapularis* in a rural New Jersey County. *Emerg. Infect. Dis.* 4: 97-99, 1998). Left unchecked, *anaplasma* infection can be a potentially fatal disease resulting from the targeting and replication of Ap within human neutrophils (Bakken J. S. et al.: *JAMA* 272: 212-218, 1994). *Anaplasma phagocytophilum* infection thus emerges as a significant healthcare concern.

Detection of *anaplasma* infection is crucial. Ideally, a diagnostic assay should be capable of detecting *anaplasma* infection at its earliest stages, when antibiotic treatment is most effective and beneficial. Traditional detection methods for *anaplasma* infection includes: (i) microscopic identification of morulae in granulocytes, (ii) PCR analysis using whole blood, (iii) isolation of the *anaplasma* bacterium from whole blood, and (iv) serological tests, particularly indirect immunofluorescence assay (IFA). Microscopic examination is tedious and prone to sampling error. PCR test is sensitive in detecting the tick-borne pathogen during the period of time when the pathogen is present in the blood of infected patients. IFA is most commonly used (Park, J., et al.: Detection of antibodies to *Anaplasma phagocytophilum* and *Ehrlichia chaffeensis* antigens in sera of Korean patients by western immunoblotting and indirect immunofluorescence assays. *Clinical and Diagnostic Laboratory Immunology* 10(6): 1059-1064, 2003), but this test often gives false positive results. Such results can be attributed in part to the use of whole-cell antigens because such proteins may be shared with other bacteria (Magnarelli, L. A., et al.: Use of recombinant antigens of *Borrelia burgdorferi* and *Anaplasma phagocytophilum* in enzyme-linked immunosorbent assays to detect antibodies in white-tailed deer. *J. Wildlife Dis.* 40(2): 249-258, 2004). When clinical symptoms are manifested or high and stable antibody titers to *Anaplasma phagocytophilum* are found in patient blood, it reaches a late infection stage and bypass the window of antibiotic treatment.

So far, there are only a few surface proteins on *anaplasma* pathogen that are used in diagnostic assay for immuno-responses (i.e., IgG and IgM responses). It is generally believed that outer membrane proteins in pathogens are target for eliciting an immuno-response because they may be the first to be exposed to immune cells of a host. Regarding the *anaplasma phagocytophilum* species, U.S. Pat. No. 6,964,855 discloses the use of an outer membrane protein and its fragments in a detection assay. U.S. Pat. No. 7,304,139 discloses a major surface protein 5 (MSP5) and its use in a diagnostic test. The '139 patent discloses a few patient's reactivity towards MSP5 and it lacks any data relating sensitivity and specificity, let alone any IgG/IgM distinction. Zhi et al. discloses cloning and expression of an outer membrane protein of 44 kDa and its use in a Western immunoblot assay (*J. Clinical Microbiology* 36(6): 1666-1673, 1998). Both MSP5 and p44 are outer membrane proteins in *Anaplasma phagocytophilum*. To the best knowledge of the inventors, there is no report on using any intracellular protein as an antigenic protein, let alone its possible use in ELISA detection for *Anaplasma phagocytophilum*.

In *Agrobacterium tumefaciens*, TIVSS consists of twelve (12) protein components. virB5 and a part of virB2 are proteins located on the outer surface of the pathogen. On the other hand, the rest of the TIVSS in *Agrobacterium tumefaciens* reside within the pathogen (See, FIG. 1). TIVSS in *Agrobacterium tumefaciens* may represent a prototype for TIVSS in other species. The number of TIVSS protein components varies among various different species in the family. TIVSS in *Agrobacterium tumefaciens* is believed to form a conduit for transportation of macromolecules (such as proteins) across the cell membrane. *Anaplasma phagocytophilum* is a phylogenetically distant species. TIVSS in *Anaplasma phagocytophilum* consists of eight (8) protein components. And the manner by which TIVSS proteins assembly and their respective functions in *Anaplasma phagocytophilum* is presently unknown. Flabio R. Araujo et al. recently reported that sera of cattle infected with *Anaplasma marginale* (a phylogenetically distant species of *Anaplasma phagocytophilum*) can recognize recombinant virB9, virB10, and elongation factor-Tu (EF-Tu). To the best of the inventor's knowledge, there is no information exists regarding the cloning and recombinant expression of the TIVSS protein components in *Anaplasma phagocytophilum*.

There is a continuing need in the discovery of a novel antigen present in *Anaplasma phagocytophilum* that may be useful in sero-detection of this pathogen. The present invention cures all the above-mentioned defects and provides a useful detection assay for *Anaplasma phagocytophilum* infection. Disclosed herein are the cloning, expression, purification, and use of a recombinant type IV secretion system (TIVSS) protein virB10 (rTIVSS virB10) and its protein fragments. Particular embodiments include the development of a diagnostic ELISA test useful for detecting IgM/IgG antibody responses to *Anaplasma phagocytophilum*. The present assay utilizes recombinant virB10 protein fragments and the data show that they can be used to discriminate *Anaplasma phagocytophilum* IFA-positive and IFA-negative patient samples with high sensitivity and specificity.

SUMMARY OF THE INVENTION

The present invention provides polypeptides of *Anaplasma phagocytophilum* that are useful in the detection of *Anaplasma phagocytophilum*. The present invention provides recombinant TIVSS protein fragments and methods of using these polypeptides in the detection of infections with *Ana-*

*plasma phagocytophilum*, which can be useful in the diagnosis of human granulocytic anaplasmosis.

In one aspect, the present invention provides an isolated polypeptide having an amino acid sequence selected from the group consisting of SEQ ID NO: 13 and SEQ ID NO: 15.

In another aspect, the present invention provides an isolated polynucleotide with nucleotide sequence set forth in SEQ ID NO: 14 or SEQ ID NO: 16.

In one aspect, the present invention provides a vector comprising the isolated polynucleotides of virB10 protein fragments. virB10 protein fragments may include virB fragments 1-5. Preferably, the vector comprises the isolated polynucleotide with nucleotide sequence set forth in SEQ ID NO: 14 or SEQ ID NO: 16. The vector may be pET. The vector may further comprise a promoter of DNA transcription operably linked to the isolated polynucleotides of interest. The vector may further comprise a promoter of DNA transcription operably linked to the isolated polynucleotides of interest. The vector may be pET, pENTR, or pCR®8/GW/TOPO®. The promoter may be a lac promoter, trp promoter or tac promoter.

In one aspect, the present invention provides a host cell comprising the vector. The host cell may be *E. coli* and the *E. coli* may include NOVABLUE K12 strain or BL21 (DE3).

In one aspect, the present invention provides a method of producing an isolated polypeptide of virB10 fragments having an amino acid set forth in SEQ ID NO: 13 or SEQ ID NO: 15. The method comprises the steps of: (i) introducing the isolated virB10 gene fragments into a host cell; (ii) growing the host cell in a culture under suitable conditions to permit production of said isolated polypeptide; and (iii) isolating the isolated polypeptide of virB10. Preferably, the virB10 gene fragments include isolated polynucleotide with nucleotide sequence set forth in SEQ ID NO: 14 or SEQ ID NO: 16.

In one aspect, the present invention provides a method of detecting the presence of an antibody against *Anaplasma phagocytophilum* in a biological sample of a mammal, comprising: (i) immobilizing an isolated polypeptide of virB10 fragments onto a surface, the amino acid sequences of virB10 are set forth in SEQ ID NO: 13 or SEQ ID NO: 15; (ii) contacting the isolated polypeptide with a patient's biological sample, under conditions that allow formation of an antibody-antigen complex between the immobilized polypeptide (antigen) and an antibody against *Anaplasma phagocytophilum*; and (iii) detecting the formation of the antibody-antigen complex; the detected antibody-antigen complex is indicative of the presence of said antibody against *Anaplasma phagocytophilum* in the biological sample. Preferably, the mammal is a human. ELISA test employs an IgG or IgM assay. Preferably, the ELISA has a sensitivity of at least >70%, and a specificity of at least >70%.

In another aspect, the present invention provides a method of diagnosing an infection of *Anaplasma phagocytophilum* in a mammal, comprising the steps of: (i) obtaining a biological sample from a mammal suspected of having an *Anaplasma phagocytophilum* infection; (ii) immobilizing an isolated polypeptide of virB10 protein fragments onto a surface, the amino acid sequences of virB10 protein fragments are set forth in SEQ ID NO: 13 or SEQ ID NO: 15; (iii) contacting the immobilized polypeptide with the biological sample, under conditions that allow formation of an antibody-antigen complex; and (iv) detecting said antibody-antigen complex. The detected antibody-antigen complex is indicative of the presence of said antibody against *Anaplasma phagocytophilum* in the biological sample. Preferably, the biological sample is whole blood, and the antibody is IgG or IgM.

In yet another aspect, the present invention provides an article of manufacture comprising a packaging material; and the isolated polypeptides of virB10 protein fragments. The article of manufacture may further comprise an instruction for detecting the presence of antibody against *Anaplasma phagocytophilum*.

BRIEF DESCRIPTION OF THE DRAWINGS

FIG. 5 depicts the Nucleotide Sequence for TIVSS virB10 Gene in *Anaplasma phagocytophilum* (accession #YP_505896) (SEQ ID NO: 10), and the deduced amino acid sequence of TIVSS virB10 protein (SEQ ID NO: 11).

FIG. 11 depicts the IgM and IgG ELISA for Recombinant virB10 of *Anaplasma phagocytophilum*.

FIG. 12 depicts the Location of Fragments 1-5 relative to the Full-Length virB10 protein.

FIG. 13 depicts the Nucleotide Sequence for TIVSS virB10 Fragment 1 (SEQ ID NO: 12), and the Deduced Amino Acid Sequence of TIVSS virB10 Fragment 1 (SEQ ID NO: 13).

FIG. 14 depicts the Nucleotide Sequence for TIVSS virB10 Fragment 2 (SEQ ID NO: 14), and the Deduced Amino Acid Sequence of TIVSS virB10 Fragment 2 (SEQ ID NO: 15).

FIG. 15 depicts the Nucleotide Sequence for TIVSS virB10 Fragment 3 (SEQ ID NO: 16), and the Deduced Amino Acid Sequence of TIVSS virB10 Fragment 3 (SEQ ID NO: 17).

FIG. 16 depicts the Nucleotide Sequence for TIVSS virB10 Fragment 4 (SEQ ID NO: 18), and the Deduced Amino Acid Sequence of TIVSS virB10 Fragment 4 (SEQ ID NO: 19).

FIG. 17 depicts the Nucleotide Sequence for TIVSS virB10 Fragment 5 (SEQ ID NO: 20), and the Deduced Amino Acid Sequence of TIVSS virB10 Fragment 5 (SEQ ID NO: 21).

FIG. 37 depicts the IgG ELISA for Recombinant virB10 Fragments 3 and 4.

DETAILED DESCRIPTION OF THE INVENTION

Figure 1:
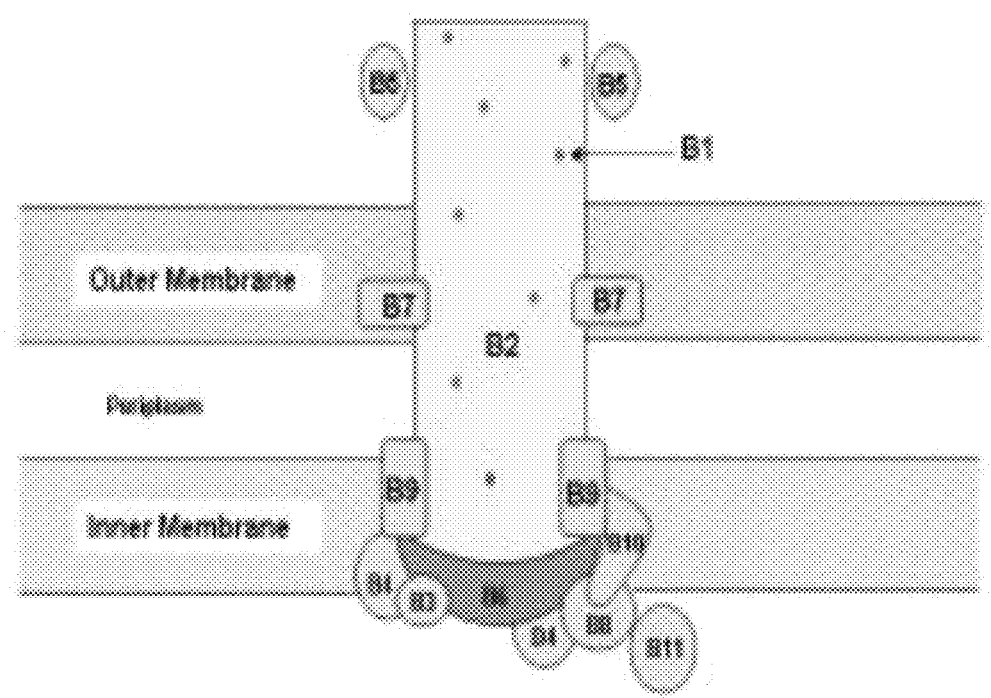
FIG. 1 schematically depicts the *Agrobacterium tumefaciens* Type IV Secretion System (TIVSS). Modified from KEGG: Kyoto Encyclopedia of Genes and Genomes (www-.genome.ad.jp/dbgetbin/get_pathway?org_name=aph&mapno=03080).
Figure 2:
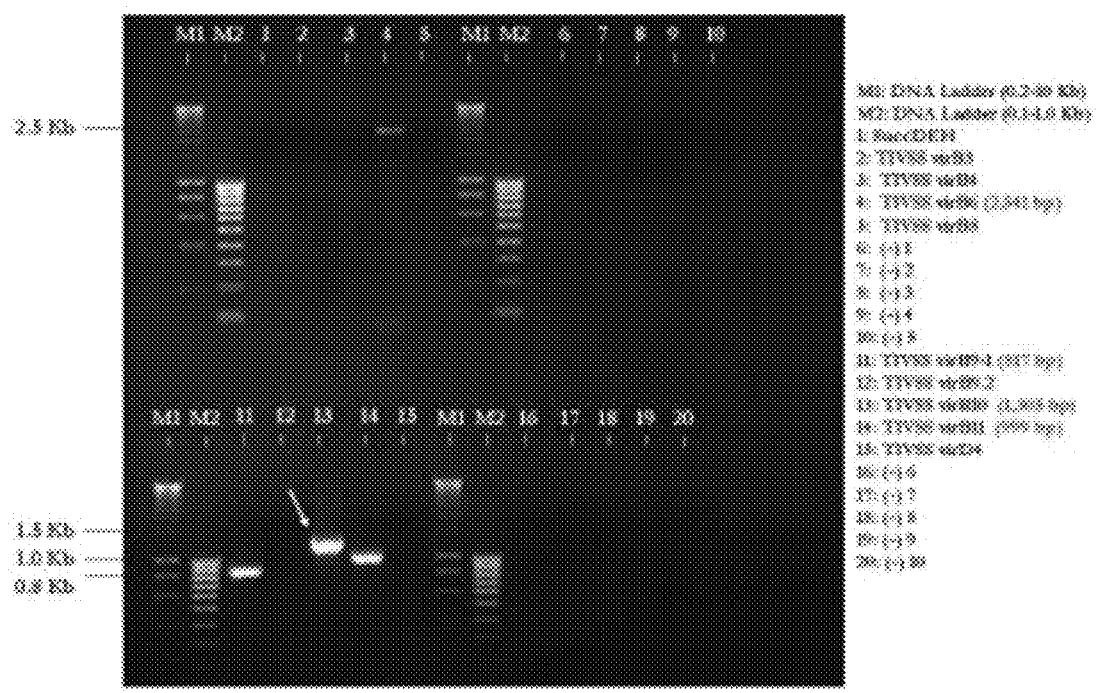
FIG. 2 depicts the EK/LIC PCR Amplification of *Anaplasma* Genes Encoding TIVSS proteins of *Anaplasma phagocytophilum*. Lane 13 depicts the full length virB10 gene (1,305 bp).
Figure 3:
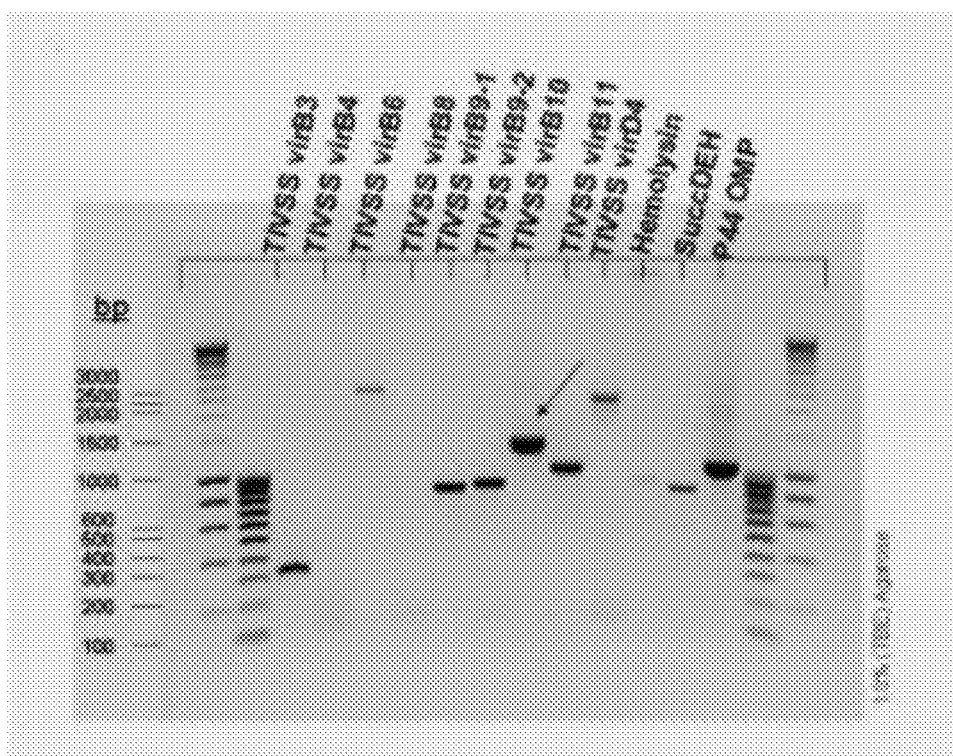
FIG. 3 depicts the Post-PCR Clean-Up of *Anaplasma* Clones for Recombinant Expression. The arrow in this figure shows the virB10 amplicon.
Figure 4:
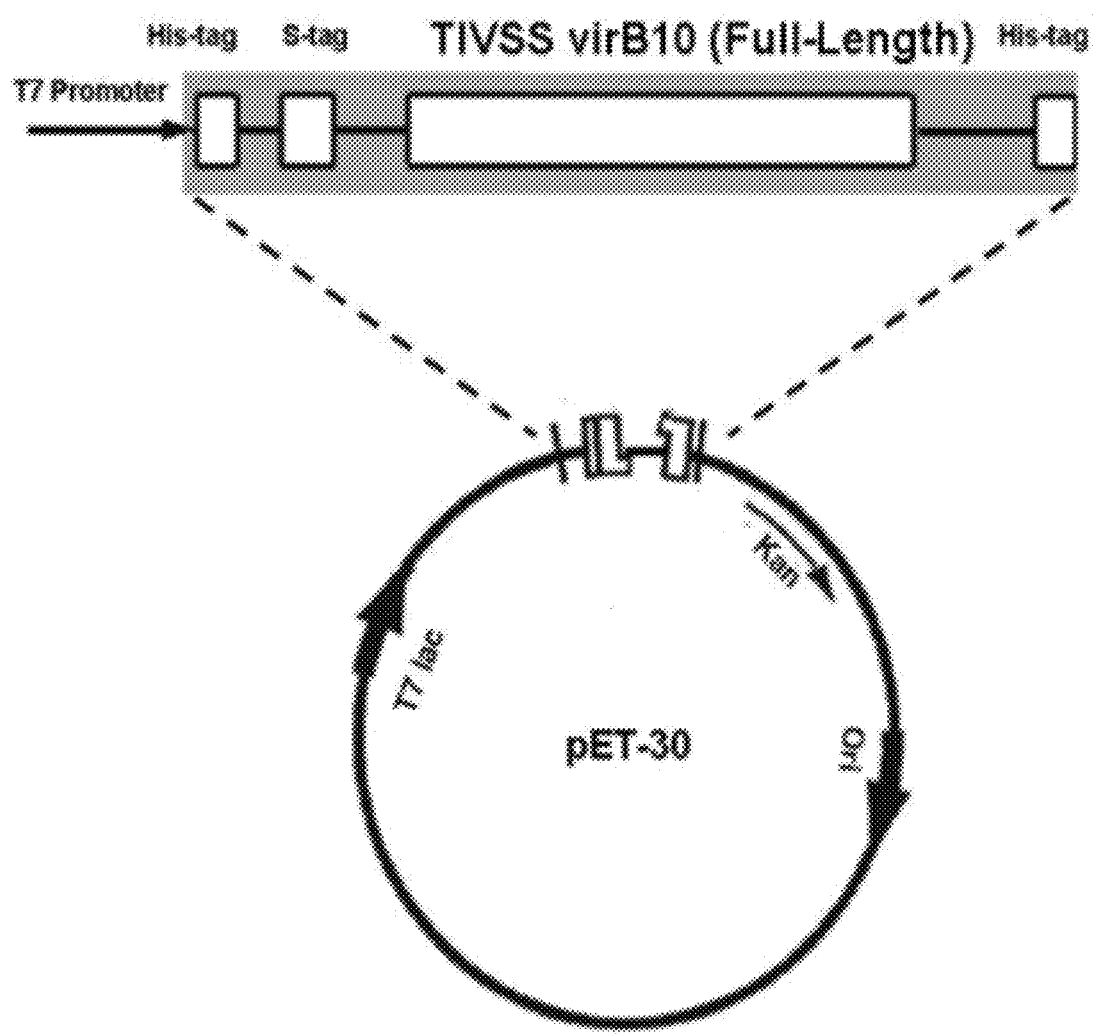
FIG. 4 depicts the pET-30 Vector Containing full-length virB10 Gene.
Figure 6:
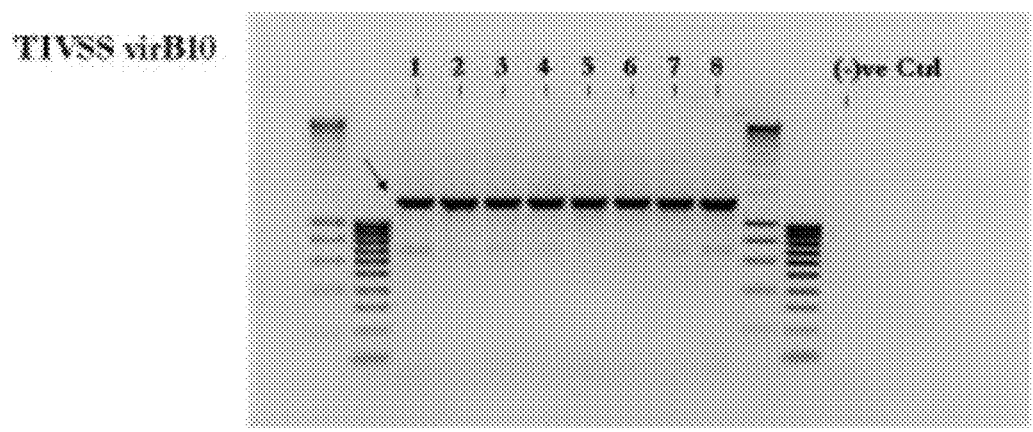
FIG. 6 depicts the Colony PCR of virB10 Transformants in NOVABLUE *E. coli*.

The present invention can be better understood from the following description of preferred embodiments, taken in conjunction with the accompanying drawings. It should be apparent to those skilled in the art that the described embodiments of the present invention provided herein are merely exemplary and illustrative and not limiting.

DEFINITIONS

Various terms used throughout this specification shall have the definitions set out herein.

As used herein, "virB10" refers to a polypeptide having an amino acid sequence as set forth in SEQ ID NO: 26 (NCBI Accession No. YP_505896). The polypeptide represents the type IV secretion system virB10 protein present in *Anaplasma phagocytophilum* strain HZ. The virB10 polypeptide is shown by the present inventors to bind to antibodies that are present in *Anaplasma* patients' sera in an ELISA assay.

As used herein, "virB10 fragments" refers to protein fragments of the full length virB10 polypeptide. The term "virB10 fragment" is intended to include at least the five (5) protein fragments of virB10 disclosed herein in this application (namely, fragment 1, fragment 2, fragment 3, fragment 4, and fragment 5). The amino acid sequences of the virB10 protein fragments are set forth below: (i) virB10 protein fragment 1 having amino acid as set forth in SEQ ID No: 13, (ii) virB10 protein fragment 2 having amino acid as set forth in SEQ ID NO: 15, (iii) virB10 protein fragment 3 having amino acid as set forth in SEQ ID NO: 17, (iv) virB10 protein fragment 4 having amino acid as set forth in SEQ ID NO: 19, and (v) virB10 protein fragment 5 having amino acid as set forth in SEQ ID NO: 21. One of ordinary skill in the art would appreciate that the virB10 protein fragments would encompass protein fragment variants (e.g., conservative substitutions of amino acids) insofar as the protein fragments still possess the ability to bind to IFA(+) sera from *Anaplasma* infected patients' sera in an ELISA assay.

As used herein, the term "ELISA" refers to "Enzyme-Linked ImmunoSorbent Assay" and is a biochemical technique used in detecting the presence of antibody or antigen in a sample.

As used herein, the term "IFA" refers to immunofluorescence assay. "IFA sero-positive sera from a patient" refers to sera (obtained from a patient) that exhibit positive immunofluorescence staining towards cells that have been infected with *Anaplasma phagocytophilum*. "IFA sero-negative sera from a patient" refers to sera (obtained from a patient) that exhibit negligible immunofluorescence staining towards cells that have been infected with *Anaplasma phagocytophilum*.

As used herein, the terms "polypeptide," "peptide," or "protein" are used interchangeably.

As used herein, the term "recombinant polypeptide" refers to a polypeptide that is recombinantly expressed by a host cell via the use of a vector that has been modified by the introduction of a heterologous nucleic acid. For purposes of the present invention, these polypeptides are intended to encompass some polypeptide variations insofar as they retain the ability to bind to antibodies present in *Anaplasma* infected patients in an ELISA assay with comparable sensitivity and specificity. One of an ordinary skill in the art would appreciate that the polypeptide variations may include (i) conservative substitutions, (ii) substitution, (iii) addition, and (iv) deletion of amino acids. It would be further appreciated that a polypeptide variant having a sufficiently high % amino acid sequence identity (e.g., >95%), when exhibited similar antibody binding activity as to the parent polypeptide, is intended to be encompassed by the present invention.

As used herein, the term "% amino acid sequence identity" is defined as the percentage of amino acid residues that are identical to the amino acid residues in the TIVSS (e.g., virB10) polypeptide or protein fragments thereof. Alignment for purposes of determining percent amino acid sequence identity can be achieved in various ways that are well within the skill in the art, for instance, using publicly available computer software such as BLAST, BLAST-2, ALIGN or Megalign (DNASTAR) software.

As used herein, the term "mammal" refers to any vertebrate of the class mammalia, having the body more or less covered with hair, nourishing the young with milk from the mammary glands, and, with the exception of the egg-laying monotremes, giving birth to live young. Preferably, the mammal is human.

As used herein, the term "primer" refers to a nucleotide sequence which can be extended by template-directed polymerization. For the purpose of this application, the term "nucleotide sequence" is intended to include DNA or modification thereof.

As used herein, the term "biological sample" may include but are not limited to blood (e.g., whole blood, blood serum, etc), cerebrospinal fluid, synovial fluid, and the like from a mammal such as a human or domestic animal. Extraction of nucleic acids from biological samples is known to those of skill in the art.

As used herein, the term "ROC" refers to Receiver Operating Characteristics Analysis. ROC analysis is a standard statistical tool for evaluation of clinical tests. ROC accesses the performance of the system in terms of "Sensitivity" and "1—Specificity" for each observed value of the discriminator variable assumed as decision threshold (i.e., cutoff value to differentiate between two groups of response). For ELISA, the cutoff value can be shifted over a range of observed values (i.e., $OD_{450}$ nm reading), and Sensitivity and 1—Specificity can be established for each of these values. The optimal pair of Sensitivity and Specificity is the point with the greatest distance in a Northwest direction.

The present invention provides recombinant and synthetic polypeptides that, when assayed in an ELISA assay, react to IFA sero-positive sera and do not react to IFA sero-negative sera from a patient infected with *Anaplasma phagocytophilum*.

Recombinant Polypeptides of TIVSS

The present invention specifically contemplates expression and preparation of recombinant and synthetic polypeptides of virB10 and protein fragments thereof, characterized by being capable of binding to antibodies present in IFA positive patient sera. In one embodiment, the present invention thus comprises the isolated nucleic acid having the nucleotide sequence set forth in FIG. 5 (SEQ ID NO: 10). The recombinant proteins of virB10 expressed by the nucleic acids described herein encompasses the protein set forth in FIG. 5 (SEQ ID NO: 11). The recombinant virB10 protein described herein possesses the ability to bind to antibodies present in IFA positive sera (and not IFA negative sera).

In another embodiment, the present invention thus comprises the isolated nucleic acid having the nucleotide sequence set forth in FIG. 13 (SEQ ID NO: 12). The recombinant proteins expressed by the nucleic acids described herein encompasses those proteins set forth in FIG. 13 (SEQ ID NO: 13).

In another embodiment, the present invention thus comprises the isolated nucleic acid having the nucleotide sequence set forth in FIG. 14 (SEQ ID NO: 14). The recombinant proteins expressed by the nucleic acids described herein encompasses those proteins set forth in FIG. 14 (SEQ ID NO: 15).

In another embodiment, the present invention thus comprises the isolated nucleic acid having the nucleotide sequence set forth in FIG. 15 (SEQ ID NO: 16). The recombinant proteins expressed by the nucleic acids described herein encompasses those proteins set forth in FIG. 14 (SEQ ID NO: 17).

In another embodiment, the present invention thus comprises the isolated nucleic acid having the nucleotide sequence set forth in FIG. 16 (SEQ ID NO: 18). The recombinant proteins expressed by the nucleic acids described herein encompasses those proteins set forth in FIG. 14 (SEQ ID NO: 19).

In another embodiment, the present invention thus comprises the isolated nucleic acid having the nucleotide sequence set forth in FIG. 17 (SEQ ID NO: 20). The recombinant proteins expressed by the nucleic acids described herein encompasses those proteins set forth in FIG. 14 (SEQ ID NO: 21).

The virB11 protein fragments described herein possess the ability to bind to antibodies present in IFA positive sera (and not IFA negative sera).

In one embodiment, the present invention provides a recombinant polypeptide containing an amino acid sequence as set forth in SEQ ID NO: 13. In another embodiment, the present invention provides a recombinant polypeptide containing an amino acid sequence set forth in SEQ ID NO: 15.

It is understood that these recombinant polypeptides encompass variants. One type of variants includes modification of amino acids of recombinant polypeptides; such as, for example, substitution, deletion, or addition of amino acids. The present invention is intended to encompass the polypeptide variants of virB10 and virB11 that retain the antibody binding ability towards IFA sero-positive sera and do not react to IFA sero-negative sera from *Anaplasma* infected patients. One of ordinary skill in the art would recognize that conservative amino acid substitutions may include simply substituting glutamic acid with aspartic acid; substituting isoleucine with leucine; substituting glycine or valine, or any divergent amino acid, with alanine, substituting arginine or lysine with histidine, and substituting tyrosine and/or phenylalanine with tryptophan. In another embodiment, addition and deletion of single amino acid may be employed. It is also appreciated by one of ordinary skill in the art that a few amino acids can be included or deleted from each or both ends, or from the interior of the polypeptide without significantly altering the peptide's ability to bind antibody (i.e., maintain high sensitivity and specificity (>70%), when tested in an ELISA assay.

Recombinant Expression of virB10 and virB11 Polypeptides: Vectors and Hosts

Transcriptional and translational control sequences are DNA regulatory sequences, such as promoters, enhancers, terminators, and the like, that provide for the expression of a coding sequence in a host cell.

A DNA sequence is "operatively linked" or "operably linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted upstream (5') of and in reading frame with the gene. A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease Si), as well as protein binding domains (consensus sequences) responsible for the binding of RNA polymerase.

In one embodiment, the present invention provides the expression of the DNA sequences disclosed herein. As is well known in the art, DNA sequences may be recombinantly expressed by operatively linking the sequences to an expression control sequence in an appropriate expression vector; and expressing that linked vector via transformation in an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence. A wide variety of host/expression vector combinations may be employed in expressing the DNA sequences of this invention. Useful expression vectors, for example, may consist of segments of chromosomal, non-chromosomal and Synthetic DNA sequences. Suitable vectors include pET, pENTR, and pCR®8/GW/TOPO® and the like. The promoter contains lac promoter, trp promoter and tac promoter.

In one embodiment, a host cell contains the vector comprising the polynucleotides of the present invention. Exemplary host cell includes *E. coli*. Various *E. coli* strains include, for example, NOVABLUE strain, BL21 (DE3) or BL21 pLsS (DE3).

It will be understood that not all vectors, expression control sequences and hosts will function equally well to express the DNA sequences of this invention. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors, a person skilled in the art will be able to construct a variety of vector/expression control sequence/host combinations that will express the DNA sequences of this invention on fermentation or in large scale animal culture.

For recombinant expression of the various proteins used in this application, genes encoding the various proteins of interest can be conveniently inserted into a cloning vector and the vector containing the gene of interest is transfected or transformed into a suitable host cell for protein expression. Various publicly available vectors may be used. For example, vectors may include a plasmid, cosmid, viral particle, or phage. Examples of vectors included pET30®, pENTR®, pCR8/GW/TOPO® and the like. Vector components generally include, but are not limited to, one or more of a signal sequence, an origin of replication, a marker gene, an enhancer element, a promoter, and a transcription termination sequence. Construction of suitable vectors containing one or more of these components as well as the gene of interest employs standard ligation techniques which are known to the skilled artisan.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Examples of suitable selectable markers for mammalian cells include those that enable the identification of cells competent to take up the antigen-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 (Stinchcomb et al., *Nature*, 282:39 (1979). The trp1 gene provides a selection marker for a mutant strain of yeast lacking the ability to grow in tryptophan, for example, ATCC No. 44076 or PEP4-1 (Jones, *Genetics*, 85:12 (1977)).

A number of promoters can be used in order to enhance the expression of the gene of interest. In one embodiment, a promoter can be employed which will direct expression of a polynucleotide of the present invention in *E. coli*. Other equivalent transcription promoters from various sources are known to those of skill in the art. Exemplary promoters include the β-lactamase and lactose promoter systems (Chang et al., Nature, 275:615 (1978)), alkaline phosphatase, a tryptophan (trp) promoter system (Goeddel, *Nucleic Acids Res.*, 8:4057 (1980)), and the like.

A promoter may be operably linked to the protein-encoding nucleic acid sequence to direct mRNA synthesis. Promoters recognized by a variety of potential host cells are well known. For example, promoters for use in bacterial systems also will contain a Shine-Dalgarno (S.D.) sequence operably linked to the DNA encoding the protein of interest.

Transcription of a DNA encoding the antigen by higher eukaryotes may be increased by inserting an enhancer sequence into the vector. Enhancers are cis-acting elements of DNA, usually about from 10 to 300 bp, that can act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the 15-kDa coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding *Anaplasma phagocytophilum* antigen.

The nucleic acid (e.g., genomic DNA) encoding recombinant *Anaplasma phagocytophilum* antigen of the present invention may be inserted into a replicable vector for cloning (amplification of the DNA) or for expression. For example, a type IV secretion system (TIVSS) protein, such as full-length virB10 (SEQ ID No. 10) may be inserted into a replicable vector for cloning and for expression of full-length virB9 protein or fragments thereof. The appropriate nucleic acid sequence may be inserted into the vector by a variety of procedures. In general, DNA is inserted into an appropriate restriction endonuclease site(s) using techniques known in the art.

Host cells are transfected or transformed with expression or cloning vectors described herein for antigen production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescens*, and *Shigella*, as well as Bacilli such as *B. subtilis* and *B. licheniformis, Pseudomonas* such as *P. aeruginosa*, and *Streptomyces*. These examples are illustrative rather than limiting.

Methods of eukaryotic cell transfection and prokaryotic cell transformation are known to the ordinarily skilled artisan, for example, $CaCl_2$, $Ca_2PO_4$, liposome-mediated and electroporation. Depending on the host cell used, transformation is performed using standard techniques appropriate to such cells. The calcium treatment employing calcium chloride, as described in Sambrook et al., or electroporation is generally used for prokaryotes. For mammalian cells without such cell walls, the calcium phosphate precipitation method of Graham and van der Eb, *Virology,* 52:456-457 (1978) can be employed. Transformations into yeast are typically carried out according to the method of Van Solingen et al., *J. Bact.,* 130:946 (1977). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, See Keown et al., Methods in Enzymology, 185:527-537 (1990). The particular selection of host/cloning vehicle combination may be made by those of skill in the art after due consideration of the principles set forth without departing from the scope of this invention (See, e.g., Sambrook et al., *Molecular Cloning, A Laboratory Manual* $2^{nd}$ edition, 1989, Cold Spring Harbor Press, NY).

The antigen may be recombinantly produced as a fusion polypeptide with a heterologous polypeptide. The heterologous polypeptide may serve as a signal sequence or other polypeptide having a specific cleavage site at the N-terminus of the mature protein or polypeptide. In general, the signal sequence may be a component of the vector, or it may be a part of the antigen-encoding DNA that is inserted into the vector. In mammalian cell expression, mammalian signal sequences may be used to direct secretion of the protein, such as signal sequences from secreted polypeptides of the same or related species, as well as viral secretory leaders. An overview of expression of recombinant proteins is found in *Methods of Enzymology* v. 185, Goeddel, D. V. ed. Academic Press (1990).

Recombinant gene expression may be measured in a sample directly, for example, by conventional Southern blotting, Northern blotting to quantitate the transcription of mRNA (Thomas, *Proc. Natl. Acad. Sci.* USA, 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Recombinant gene expression, alternatively, may be measured by immunological methods, such as immunohistochemical staining of cells or tissue sections and assay of cell culture or body fluids, to quantitate directly the expression of gene product. Antibodies useful for immunohistochemical staining and assay of sample fluids may be either monoclonal or polyclonal, and may be prepared in any mammal. Conveniently, the antibodies may be prepared against a native sequence polypeptide or against a synthetic peptide based on the DNA sequences provided herein or against exogenous sequence fused to *Anaplasma phagocytophilum* DNA and encoding a specific antibody epitope.

After expression, recombinant antigen may be recovered from culture medium or from host cell lysates. If membrane-bound, it can be released from the membrane using a suitable detergent solution (e.g. TRITON-X 100) or by enzymatic cleavage. Cells employed in expression of *Anaplasm phagocytophilum* antigen can be disrupted by various physical or chemical means, such as freeze-thaw cycling, sonication, mechanical disruption, or cell lysing agents.

It may be desired to purify recombinant antigen from host cell proteins. The following procedures are exemplary of suitable purification procedures: by fractionation on an ion-exchange column; reverse phase HPLC; chromatography on silica or on a cation-exchange resin such as DEAE; chromatofocusing; SDS-PAGE; ammonium sulfate precipitation; metal chelating columns to bind epitope-tagged forms of the protein of interest. Various methods of protein purification may be employed and such methods are known in the art and described for example in Deutscher, *Methods in Enzymology,* 182 (1990); Scopes, Protein Purification: Principles and Practice, Springer-Verlag, New York (1982). The purification step(s) selected will depend, for example, on the nature of the production process used and the particular antigen produced.

ELISA Assay

Detection of antibody binding in IFA sero-positive sera may be accomplished by techniques known in the art, e.g., ELISA (enzyme-linked immunosorbent assay), western blots, and the like. In one embodiment, antibody binding is assessed by detecting a label on the primary antibody. In another embodiment, the primary antibody is assessed by detecting binding of a secondary antibody or reagent to the primary antibody. In a further embodiment, the secondary antibody is labeled. Many means are known in the art for detecting binding in an immunoassay and are within the scope of the present invention. For example, to select specific epitopes of recombinant or synthetic polypeptide, one may assay antibody binding in an ELISA assay wherein the polypeptides or its fragments containing such epitope.

As appreciated by one skilled in the art, an enzyme-linked immunosorbent assay (ELISA) may be employed to detect antibody binding in IFA sero-positive sera. In an initial step of an ELISA, an antigen is immobilized onto a surface (for example by passive adsorption known as coating). For purposes of this application, exemplary antigens include *Anaplasma phagocytophilum* type IV secretion system proteins (eg. virB10 and virB11), hemolysin, succinate dehydrogenase and p44-8 outer membrane protein and the like. Recombinant full-length protein as well as fragments thereof may be used. Immobilization of antigen may be performed on any inert support that is useful in immunological assays. Examples of commonly used supports include small sheets, SEPHADEX and assay plates manufactured from polyethylene, polypropylene or polystyrene. In a preferred embodiment the immobilized antigens are coated on a microtiter plate that allows analysis of several samples at one time. More preferably, the microtiter plate is a microtest 96-well ELISA plate, such as those sold under the name NUNC MAXISORP or IMMULON.

Antigen immobilization is often conducted in the presence of a buffer at an optimum time and temperature optimized by one skilled in the art. Suitable buffers should enhance immobilization without affecting the antigen binding properties. Sodium carbonate buffer (e.g., 50 mM, pH 9.6) is a representative suitable buffer, but others such as Tris-HCl buffer (20 mM, pH 8.5), phosphate-buffered saline (PBS) (10 mM, pH 7.2-7.4) are also used. Optimal coating buffer pH will be dependent on the antigen(s) being immobilized. Optimal results may be obtained when a buffer with pH value 1-2 units higher than the isoelectric point (pI) value of the protein is used. Incubation time ranges from 2-8 hours to overnight. Incubation may be performed at temperatures ranging from 4-37° C. Preferably, immobilization takes place overnight at 4° C. The plates may be stacked and coated long in advance of the assay itself, and then the assay can be carried out simultaneously on several samples in a manual, semi-automatic, or automatic fashion, such as by using robotics.

Blocking agents are used to eliminate non-specific binding sites in order to prevent unwanted binding of non-specific antibody to the plate. Examples of appropriate blocking agents include detergents (for example, TWEEN-20, TWEEN-80, TRITON-X 100, sodium dodecyl sulfate), gelatin, bovine serum albumin (BSA), egg albumin, casein, non-fat dried milk and the like. Preferably, the blocking agent is BSA. Concentrations of blocking agent may easily be optimized (e.g. BSA at 1-5%). The blocking treatment typically takes place under conditions of ambient temperatures for about 1-4 hours, preferably 1.5 to 3 hours.

After coating and blocking, sera from the control (IFA sero-negative) or IFA sero-positive patients are added to the immobilized antigens in the plate. Biological sample (i.e., sera) may be diluted in buffer. Phosphate Buffered Saline (PBS) containing 0.5% BSA, 0.05% TWEEN 20® detergent may be used. TWEEN 20® acts as a detergent to reduce non-specific binding.

The conditions for incubation of the biological sample and immobilized antigen are selected to maximize sensitivity of the assay and to minimize dissociation. Preferably, the incubation is accomplished at a constant temperature, ranging from about 0° C. to about 40° C., preferably from about 22 to 25° C. to obtain a less variable, lower coefficient of variant (CV) than at, for example, room temperature. The time for incubation depends primarily on the temperature, being generally no greater than about 10 hours to avoid an insensitive assay. Preferably, the incubation time is from about 0.5 to 3 hours, and more preferably 1.5-3 hours at room temperature to maximize binding to immobilized capture antigen.

Following incubation of the biological sample and immobilized antigen, unbound biological sample is separated from the immobilized antigen by washing. The solution used for washing is generally a buffer ("washing buffer") with a pH determined using the considerations and buffers described above for the incubation step, with a preferable pH range of about 6-9. Preferably, pH is 7. The washing may be done three or more times. The temperature of washing is generally from refrigerator to moderate temperatures, with a constant temperature maintained during the assay period, typically from about 0-40° C., more preferably about 4-30° C. For example, the wash buffer can be placed in ice at 4° C. in a reservoir before the washing, and a plate washer can be utilized for this step.

Next, the immobilized capture antigen and biological sample are contacted with a detectable antibody at a time and temperature optimized by one skilled in the art. Detectable antibody may include a monoclonal antibody or a polyclonal antibody. These antibodies may be directly or indirectly conjugated to a label. Suitable labels include moieties that may be detected directly, such as fluorochrome, radioactive labels, and enzymes, that must be reacted or derivatized to be detected. Examples of such labels include the radioisotopes $^{32}P$, $^{14}C$, $^{125}I$, $^{3}H$ and $^{131}I$, fluorophores such as rare earth chelates or fluorescein and its derivatives, rhodamine and its derivatives, horseradish peroxidase (HRP), alkaline phosphatase, and the like. Preferably, the detection antibody is a goat anti-human IgG polyclonal antibody that binds to human IgG and is directly conjugated to HRP. Incubation time ranges from 30 minutes to overnight, preferably about 60 minutes. Incubation temperature ranges from about 20-40° C., preferably about 22-25° C., with the temperature and time for contacting the two being dependent on the detection means employed.

The conjugation of such labels to the antibody, including the enzymes, is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166.

Because IgG may occasionally interfere in IgM detection assays, IgG in patient sera may be removed prior to IgM ELISA. Ideally, an anti-human IgG antibody is used to neutralize the IgG in human sera. Commercial reagents such as GullSORB™ (Meridian Bioscience, Inc., Cincinnati, Ohio) may be used. The method for IgG removal can be conveniently optimized by one of ordinary skill in the art. For example, human sera can be incubated with anti-human IgG antibody prior to the IgM ELISA assay.

Diagnostic Kits Employing Recombinant virB10 Polypeptide

The present invention provides a kit for the diagnosis of *anaplasma* infection. In one embodiment, the kit is an ELISA kit containing recombinant polypeptides described herein, detection reagents including primary or secondary antibodies, and other necessary reagents including enzyme substrates and color reagents. Additional components that may be present within such kits include an instruction detailing the detection procedure for *Anaplasma phagocytophilum*, using the recombinant polypeptides of the present invention. The diagnostic kit of the present invention further comprises a positive and negative serum control. The diagnostic kit of the present invention can also be used in diagnosing other infectious diseases involving *Anaplasma phagocytophilum* such as Human Granulocytic Anaplasmosis (HGA).

The following Examples are offered by way of illustration and not by way of limitation.

EXPERIMENTAL STUDIES

Example 1

Type IV Secretion System in *Anaplasma phagocytophilum*

FIG. 1 is a schematic depiction of the Type IV Secretion System (TIVSS) in plant pathogen *Agrobacterium tumefa-*

*ciens* (modified from Kyoto Encyclopedia of Genes and Genomes (KEGG) url: <genome.ad.ip/dbgetbin/get_pathway?org_name=aph&mapno=03080>). TIVSS is believed to form a conduit for transportation of macromolecules such as proteins and DNA across the cell membrane. TIVSS in *Agrobacterium tumefaciens* represents a prototype, albeit the protein components within the TIVSS may vary among the different pathogens. For example, while *Agrobacterium* spp. have twelve (12) proteins (See, FIG. 1), *Anaplasma phagocytophilum* (a phylogenetically distant species) contains only eight (8) proteins. Notably, virB1, virB2, virB5 and virB7 are absent in *Anaplasma phagocytophilum*. The exact structural organization of TIVSS in *Anaplasma phagocytophilum* is presently unclear.

TIVSS is essential for establishing infection in *Anaplasma phagocytophilum*. There is no information about the immunogenicity of the various TIVSS proteins during the *anaplasma* infection. So far in *Anaplasma phagocytophilum*, a non-TIVSS protein (p44; a surface protein, also known as p44-8) is known to induce an antibody response in a human host (Ijdo, J. W. et al., Cloning of the gene encoding the 44-kilodalton antigen of the agent of human granulocytic ehrlichiosis and characterization of the humoral response. *Infection and Immunity*, 66(7): 3264-3269, 1998).

The present inventors surprisingly discovered that virB10 (a TIVSS protein components) and protein fragments thereof are good candidate biomarkers for the diagnosis of *Anaplasma phagocytophilum* infection. Evidence is presented herein to demonstrate that recombinantly expressed virB10 and protein fragments thereof, when immobilized in an ELISA assay, are good detection marker for an IgG/IgM antibody response to *Anaplasma phagocytophilum* infection. Specifically, virB10 fragments xy are good antigens for ELISA assay in detecting *Anaplasma phagocytophilum*.

Example 2

Cloning and Expression of virB10

I) PCR Amplification and Ligation into Plasmid Vector

We sought to determine if virB10 possesses antibody recognition sites. First we cloned and recombinantly expressed the full-length virB10 protein in *Anaplasma phagocytophilum*.

Our cloning strategy involved the design and preparation of synthetic oligonucleotides (~30 bp in length) and use of them in amplifying the virB10 gene. As controls, we also cloned two (2) non-TIVSS proteins (i.e., succinate dehydrogenase iron-sulfur subunit and p44 outer membrane protein) and used them for as comparison. Table 1 shows the nucleotide sequence of the various oligonucleotides (i.e., SEQ ID Nos. 1-6) used in the PCR amplification reaction.

Genomic DNA of *Anaplasma phagocytophilum* (a generous gift from Dr. S. Dumler at Johns Hopkins University) was used as the template for each of the PCR reactions. Synthetic oligonucleotides corresponding to the virB10 gene were used for the PCR amplification reactions. Using the synthetic oligonucleotides (sequence listed in Table 1) and genomic DNA from *Anaplasma phagocytophilum*, we successfully amplified the virB10 gene; as well as two (2) non-TIVSS genes (i.e., succinate dehydrogenase iron-sulfur and p44 proteins) (See, FIGS. 2 and 3).

FIG. 2 shows an agarose gel of the amplified genes prior to processing of the PCR reactions in preparation for ligation into pET30 vector. The virB10 amplicon having an expected size (~1.0 kb) is shown by the arrow in this figure. In preparation for ligation with the vector, the PCR amplification reactions were treated to remove any remaining nucleotides, primers, and reaction components.

FIG. 3 shows a COOMASSIE-stained gel of the amplified genes following clean-up of the PCR reactions. The arrow in this figure shows the virB10 amplicon of expected size (~1.0 Kb).

The resulting PCR products were then treated with T4 DNA polymerase and ligated into pET30 using standard protocols (See, FIG. 4). Ligation of the virB10 insert DNA (including succinate dehydrogenase iron-sulfur and p44 protein insert DNAs) was performed as described below.

II) T4 Polymerase Treatment of PCR Products and Ligation into pET30 Vector

In order to ligate the cloned insert DNA with the plasmid vector, it is necessary to create compatible ends between the amplicon and the chosen vector (e.g., pET30 Ek/LIC). We generated overhangs compatible with the Ek/LIC cloning vector on the insert DNA by T4 DNA polymerase treatment of the PCR amplicon. We ligated the treated amplicon into the expression vector to form pET30/insert DNA.

FIG. 4 depicts the pET30 vector containing the inserted gene (e.g., full-length virB10, succinate dehydrogenase iron-sulfur and p44). The nucleotide sequences of virB10, succinate dehydrogenase iron-sulfur and p44 are publicly available and their accession numbers are listed in Table 2.

III) Transformation of Recombinant Clones into NOVABLUE *E. coli*

In these series of experiments, we transformed the ligated DNAs (annealing reaction) into host bacterial cells (NOVABLUE *E. coli*). The ligated DNA was virB10 amplicons as well as succinate dehydrogenase iron-sulfur and p44 amplicons. We chose NOVABLUE *E. coli* because this bacterial strain is optimized for producing a stable cell line containing a recombinant insert (see, NOVABLUE Ek/LIC manual).

Transformation into NOVABLUE competent *E. coli* (Novagen) was performed using standard protocols. First, appropriate numbers of 20 μl aliquots of competent cells were prepared from −80° C., and allowed to thaw on ice for several minutes, followed by the addition of 1 μl of the annealing reaction and gentle stirring. The mixture was further incubated on ice for an additional 5 minutes, followed by heating the tubes for 30 seconds in a 42° C. water bath. The tubes were immediately placed on ice for 2 minutes. SOC (Super Optimal broth with Catabolite repression medium, containing 2% w/v bacto-tryptone, 0.5% w/v bacto-yeast extract, 10 mM NaCl, 2.5 mM KCl, 10 mM $MgCl_2$, 20 mM glucose) (at room temperature) was added into the tubes, and the reactions were further incubated for 1 hour at 37° C. with shaking (250 rpm). Cells were plated onto LB agar plates (containing kanamycin) and incubated at 37° C. overnight.

IV) Colony PCR of NOVABLUE Transformants

To confirm the successful transformation of insert DNA (pET30/insert DNA) in *E. coli* cells, we selected several colonies of each transformant grown on LB plates (with kanamycin), and performed colony PCR using the same set of Ek/LIC primers as in the amplification of the genes from the *Anaplasma* genomic DNA. An aliquot of each PCR reaction was analyzed using agarose gel electrophoresis.

For illustration purposes, FIG. 6 shows agarose gel electrophoresis analysis of eight of virB10 transformants in NOVABLUE *E. coli*. Amplicons of expected size (1,100 bp) (arrow) were observed following analysis of the PCR reactions. NOVABLUE *E. coli* colonies containing the pET30/insert DNA were further cultured in LB-kanamycin broth (for the isolation of plasmids).

V) Plasmid Mini-Preps In order to confirm the presence and sequence accuracy of the cloned insert DNA in the pET30 vector, we performed sequence analysis on the recombinant plasmids. The sequence analysis also provides information that the insert was in-frame of the upstream His-tag sequence. First, we isolated plasmid DNA from the transformed E. coli. WIZARD Plus SV Minipreps DNA Purification system (PROMEGA) was used according to the manufacturer's recommended protocol. The concentration (1 $OD_{260/280}$=0.5 mg/ml) and the relative purity ($OD_{260/280}$) of the isolated plasmid DNA preparations were determined by spectrophotometric analysis.

VI) Sequencing Analysis of Insert DNA

We next performed sequence analysis on the isolated plasmid DNA using the APPLIED BIOSYSTEMS 3130 Genetic Analyzer DNA Sequencing instrument. All of the insert DNA were confirmed to be accurate by BLAST analysis and in-frame. As examples, the sequence analysis of the isolated plasmid DNA for virB10 is summarized in FIG. 5. FIG. 5 depicts polynucleotide sequence encoding virB10, together with its deduced amino acid sequence. BLAST (Basic Local Alignment Search Tool, url: <blast.ncbi.nlm.nih.gov/Blast.cgi>) analysis of the sequences confirmed a match between each of the nucleotide sequences and the published sequences of the respective *Anaplasma phagocytophilium* genes.

VII) Transformation of BL21 (DE3) E. coli with Recombinant Plasmids

After confirmation of the obtained recombinant plasmids, we proceeded to transform them into BL21 (DE3) competent E. coli (Novagen). Transformation was carried out by removing the appropriate number of 20 µl aliquots of competent cells from −80° C., allowing the tubes to thaw on ice for several minutes, followed by the addition of 1 µl of the plasmid preparation to the cells with gentle stirring. The mixture was incubated on ice for 5 minutes, followed by heating of the tubes for exactly 30 seconds in a 42° C. water bath. The tubes were immediately placed on ice for 2 min. SOC (room temperature) was added, and the reactions were further incubated at 37° C. for 1 hour at 250 rpm. Cells were then plated onto LB agar plated (containing kanamycin) and incubated at 37° C. overnight.

VIII) Colony PCR of BL21 (DE3) Transformants

Figure 7:
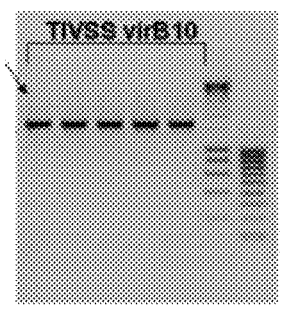
FIG. 7 depicts the Colony PCR of virB10 Transformants in BL21 (DE3) *E. coli*.

To confirm the successful transformation of recombinant pET30/insert DNA in BL21 (DE3) E. coli cells, we selected several colonies of each transformant grown on LB plates (with kanamycin), and performed colony PCR using forward and reverse vector-specific primers. An aliquot of each PCR reaction was analyzed using agarose gel electrophoresis. FIG. 7 shows agarose gel electrophoresis analysis of five (5) of virB10 transformants in BL21 (DE3) E. coli. Amplicons of expected size (~1,100 bp) (arrow) were observed following analysis of the PCR reactions. Several BL21 (DE3) E. coli colonies containing the pET30/insert DNA were then processed for recombinant expression.

In addition to virB10, we also confirmed the successful transformation of recombinant pET30/insert DNA for control inserts (i.e., succinate dehydrogenase iron-sulfur and p44).

IX) Expression of Recombinant virB10 Protein in E. coli

Figure 8:
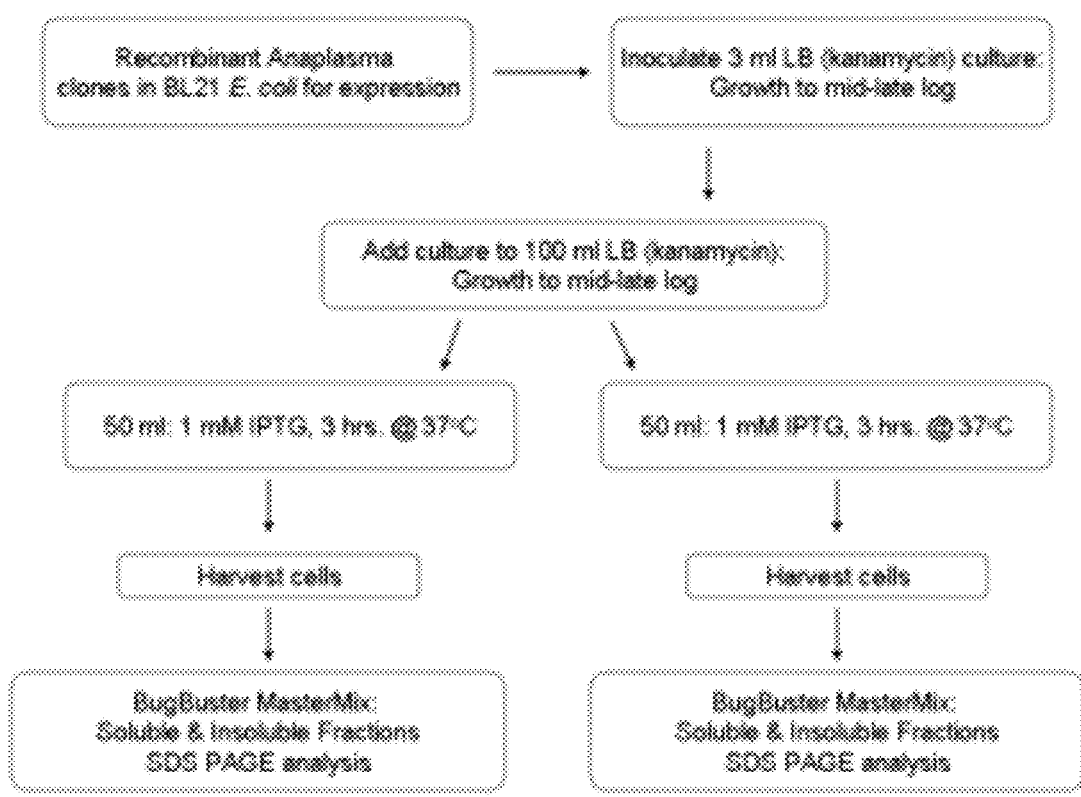
FIG. 8 depicts the protocol for IPTG-Induced Recombinant TIVSS Protein (i.e., virB10) Expression in BL21 *E. coli*.
Figure 9:
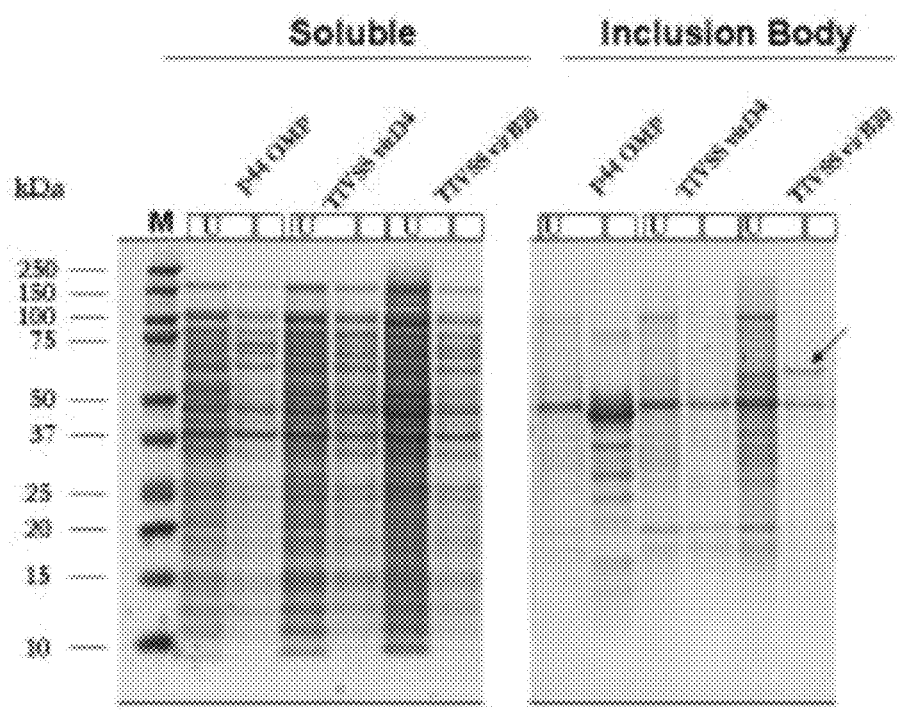
FIG. 9 depicts the IPTG Induction of TIVSS Proteins (including virB10) (Soluble v. Insoluble Fractions).

FIG. 8 depicts a flow chart depicting the steps for IPTG induction of recombinant TIVSS proteins in BL21 E. coli. For expression of recombinant TIVSS (rTIVSS) protein virB10 and non-TIVSS proteins (for example, succinate dehydrogenase iron-sulfur submit and p44), BL21 (DE3) E. coli were transformed with the pET30-rTIVSS plasmid DNA containing the respective genes.

The expression was induced with IPTG as follows: 3 ml of LB broth cultures with kanamycin (30 µg/ml final concentration) were inoculated with BL21 transformed with pET30-rTIVSS plasmid. Cultures were grown to mid-log phase ($OD_{600}$=0.5) at 37° C. with shaking at 250 rpm. When the cultures reached mid-log, the entire 3 ml was added to 100 ml LB broth with kanamycin (30 µg/ml final concentration) and allowed to grow to mid-late log phase ($OD_{600}$=0.5-1). When the cultures reached mid-late log stage, they were split into two separate 50 ml batches in 250 ml flasks. To one flask, 500 µl of IPTG was added (final concentration of 1 mM). No IPTG was added to the other flask which served as a control for assessing induction. Growth of the IPTG and control cultures was allowed to proceed for 3-3.5 hours at 37° C. with shaking (250 rpm). Cell pellets were then harvested by centrifugation at 3,000 rpm for 15 minutes at 4° C., and subsequently processed with BUGBUSTER Master Mix (Novagen) as described below.

X) Isolation and Purification of Recombinant virB10 and P44 Proteins

Isolation of the expressed recombinant virB10 protein was performed using BUGBUSTER Master Mix (Novagen) according to the manufacturer's protocol. After IPTG induction, bacterial cells were harvested from liquid cultures by centrifugation at 3,000 rpm for 15 minutes. Recombinant virB10 protein was isolated both from supernatant and cell pellets. Cell pellets were re-suspended in 5 ml of BUGBUSTER Master Mix (Novagen) by gentle vortexing. The resulting cell suspensions were incubated on a rotating mixer for 20 minutes at room temperature. The mixtures were centrifuged at 4° C. for 20 minutes at 16,000×g to remove the insoluble cellular debris. The supernatant was transferred to a fresh tube for SDS PAGE analysis. The pellet was then processed to isolate the insoluble cytoplasmic fraction, which consists of cell debris and aggregated protein (inclusion bodies). Inclusion body purification was carried out by re-suspending the pellet in the same volume (5 ml) of 1× BUGBUSTER Master Mix used to re-suspend the original cell pellet. The mixtures were vortexed, followed by the addition of 20 ml of 1:10 diluted BUGBUSTER Master Mix. The suspensions were vortexed, and then centrifuged at 5,000×g for 15 minutes at 4° C. to collect the inclusion body fraction. The pellets were re-suspended in 15 ml of 1:10 diluted BUGBUSTER Master Mix, vortexed, and centrifuged at 5,000×g for 15 min. at 4° C. This step was repeated, with the centrifugation carried out for 15 minutes at 16,000×g. The supernatant was discarded, and the pellets re-suspended in 500 µl of PBS. An aliquot of the purified inclusion body fraction was analyzed on an SDS PAGE gel.

Figure 10:
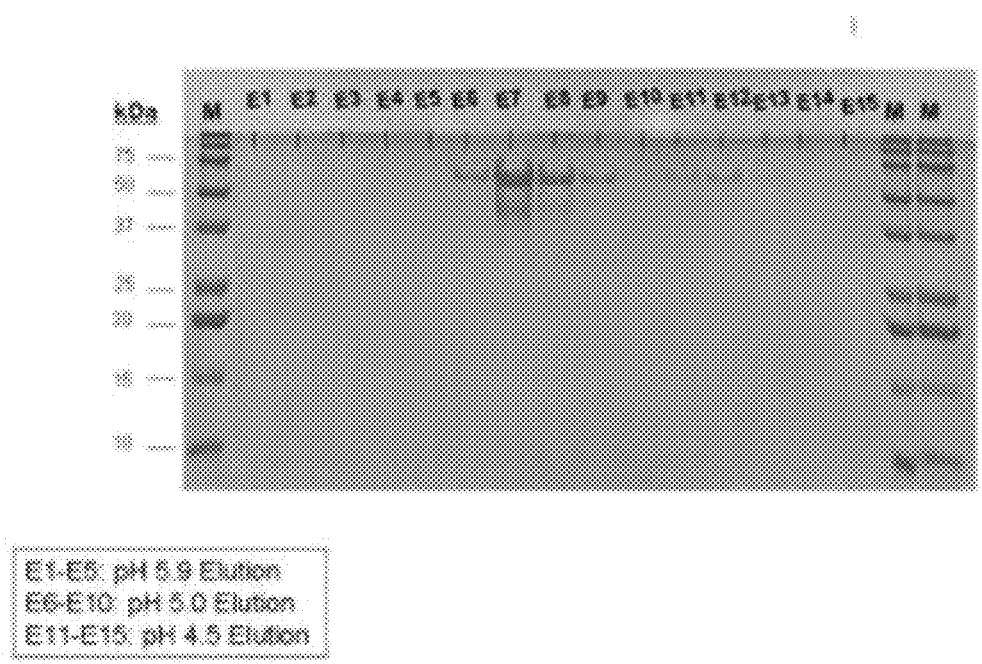
FIG. 10 depicts the Ni-NTA Purification of 6×His-Tagged Recombinant TIVSS virB10 Protein.
Figure 11A:
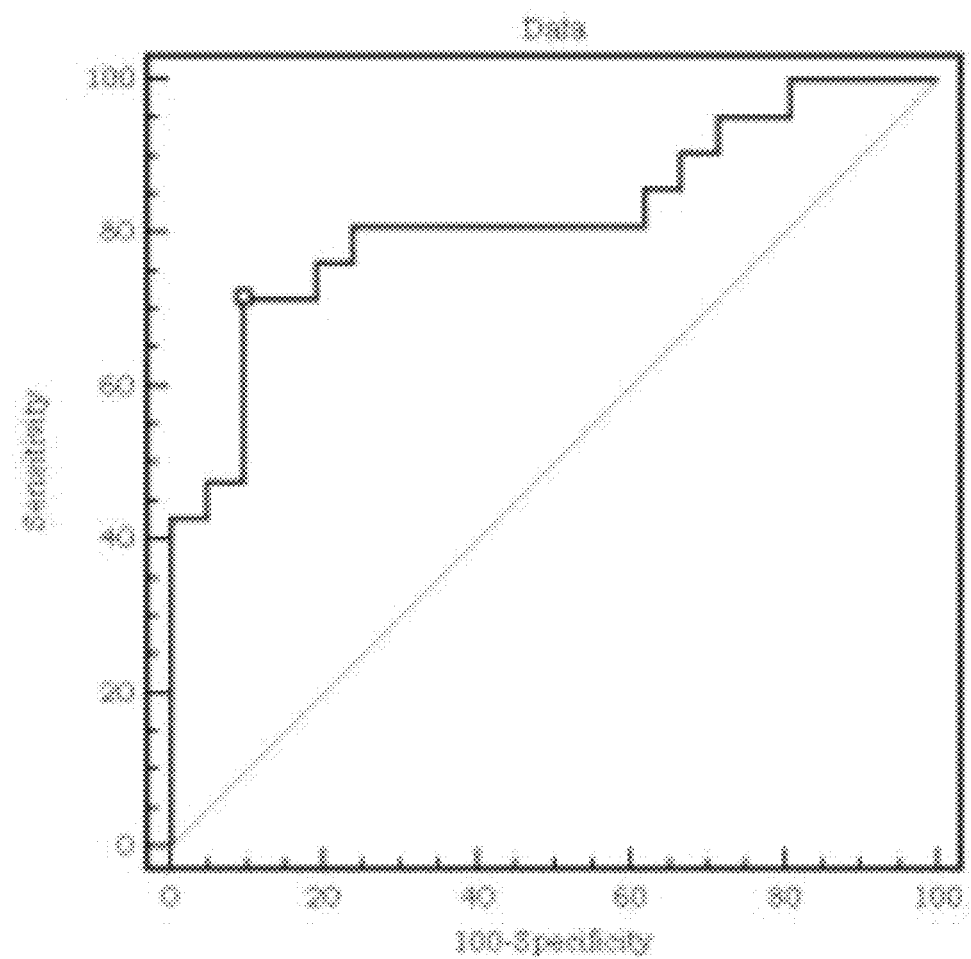
FIG. 11a depicts the ROC analysis for Recombinant virB10 IgM ELISA.

(XI) Purification of Recombinant virB10 and P44 Proteins Under Urea Denaturing Conditions The recombinant proteins present within the inclusion body pellets were re-suspended in 4 ml of denaturing lysis/binding buffer. To this mixture was added 1 ml of Ni-NTA His■Bind slurry (Novagen). The suspension was mixed gently on a rotating shaker for 1 hour. The lysate-resin mixture was carefully loaded onto a column placed over a 15 ml conical tube, and the flow-through collected and saved for later analysis. The column was washed with 4 ml of wash buffer collected in another 15 ml conical tube, and the fraction saved for later analysis. The column was washed again with 4 ml of wash buffer, and the fraction saved for later analysis. The recombinant protein was eluted with 5×0.5 ml of elution buffer (pH 5.9) (labeled as E1-E5 in FIG. 10), 5×0.5 ml of elution buffer (pH 5.0) (labeled as E6-E10 in FIG. 10), and 5×0.5 ml of elution buffer (pH 4.9) (labeled as E11-E15 in FIG. 10).

The following buffers were prepared immediately prior to being used:

Lysis Buffer with Urea
100 mM Phosphate buffer
10 mM Tris-Cl
8 M urea

Buffer pH adjusted to 8.0
Wash Buffer with Urea
100 mM Phosphate buffer
10 mM Tris-Cl
8 M urea
Buffer pH adjusted to 6.3
Elution Buffer with Urea (pH 5.9)
100 mM Phosphate buffer
10 mM Tris-Cl
8 M urea
Buffer pH adjusted to 5.9
Elution Buffer with Urea (pH 5.0)
100 mM Phosphate buffer
10 mM Tris-Cl
8 M urea
Buffer pH Adjusted to 5.0
Elution buffer with urea (pH 4.5)
100 mM Phosphate buffer
10 mM Tris-Cl
8 M urea
Buffer pH adjusted to 4.5

Example 3

IgG/IgM ELISA for Recombinantly Expressed virB10 Protein

We adopted IgG and IgM ELISA assays and evaluated the binding activity of the recombinant proteins towards IgG and IgM. The ELISA procedure involves: (i) coating 96-well micro-titer plates with the recombinant protein at varying concentrations at 4° C. overnight; (ii) adding 5% non-fat milk to block non-specific binding; (iii) adding patients' sera to allow formation of antibody-antigen complex; (iv) detecting the antibody-antigen complex. IFA sero-positive sera served as positive controls, and IFA sero-negative sera served as negative controls. Detection of antibody-antigen complex was performed with the use of horseradish peroxidase.

Patient Study: virB10

IgM ELISA

In these series of studies, we examined recombinant virB10 in an IgM ELISA. Recombinant virB10 protein exhibited a dose-dependent increase in binding towards IgM sero-positive serum (as measured by $OD_{450}$ nm). IgM ELISA for recombinant virB10 attained a 71.4% sensitivity (FIG. 17) and 90.5% specificity, both of which satisfies the threshold ($\geq$70%) required by industry.

IgG ELISA

Recombinant virB10 protein, when tested in an IgG ELISA, exhibited a dose-dependent increase in binding towards IgG sero-positive serum as measured by $OD_{450}$ nm. However, the binding levels attained (i.e., 52.4% sensitivity) were below the threshold ($\geq$70%) levels required. IgG ELISA for recombinant virB10 has a specificity of 85.7%, which is within the acceptable range ($\geq$70%) (See, FIG. 17).

ROC Analysis

The raw IgM ELISA data was analyzed with ROC curve determination using MedCalc statistical software. Performance analysis of ROC curve is shown in FIG. 17*a*. AUC of recombinant virB10 is 0.821 (95% confidence interval; range: 0.672-0.922).

Example 4

Amplification and Cloning of virB10 Protein Fragments

I) PCR Amplification and Ligation into Plasmid Vector

Figure 12:
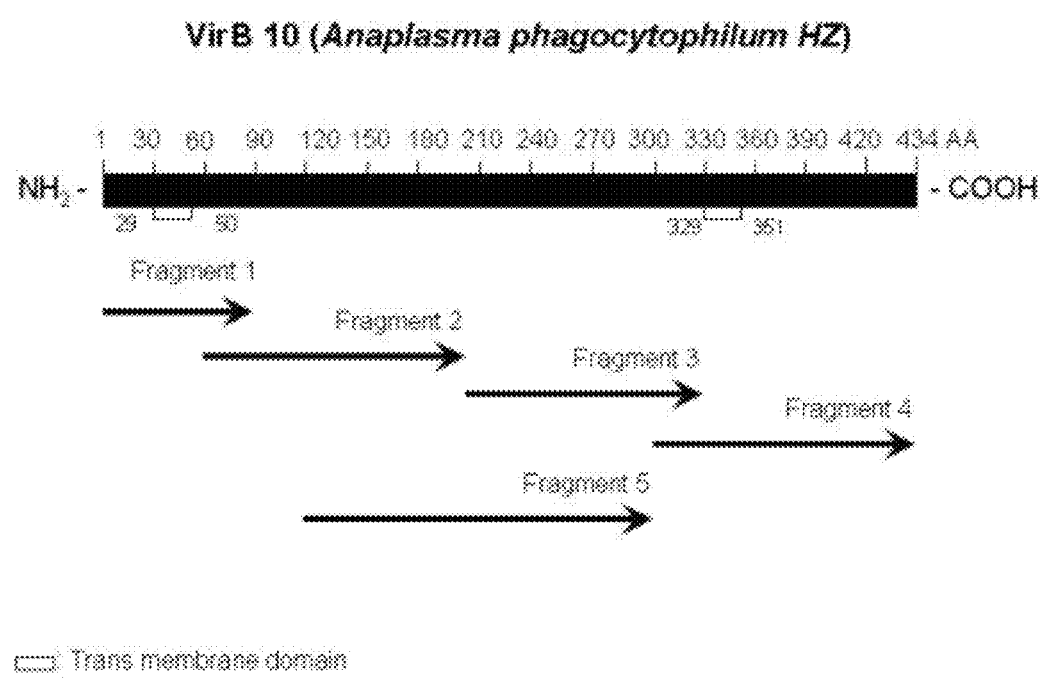
Figure 18:
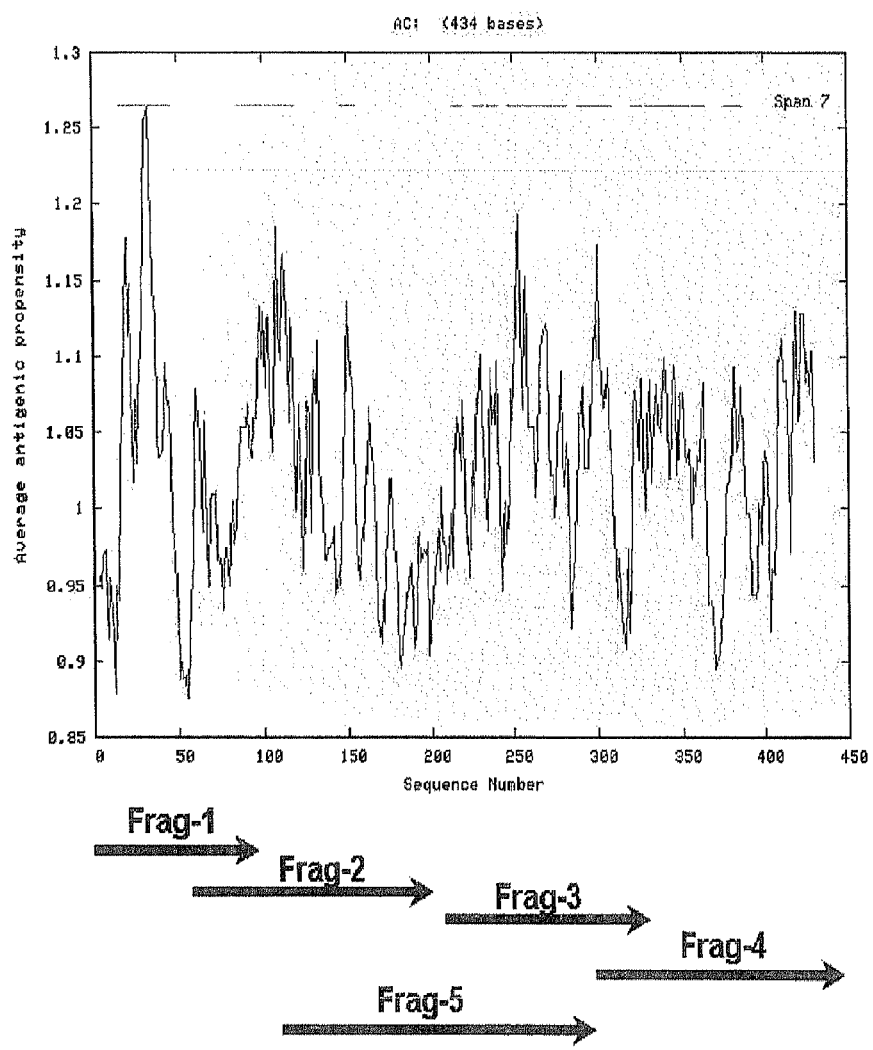
FIG. 18 depicts the Antigenicity Plot of virB10 and the Location of Fragments 1-5 (Shown Below the Plot) Relative to the Antigenic Profile of Full Length virB10 Protein.

We cloned and recombinantly expressed in *E. coli* various virB10 protein fragments; namely protein fragments 1-5. Using the antigenicity plot for full-length virB10 (See, FIG. 18), we designed oligonucleotides to amplify 5 (five) fragments encompassing regions of the protein predicted to be antigenic. The location of these fragments relative to that of the full-length virB10 protein is shown in FIG. 12. The nucleotide (SEQ ID No. 12) and amino acid (SEQ ID No. 13) sequences of fragment-1 are shown in FIG. 13. The nucleotide (SEQ ID No. 14) and amino acid (SEQ ID No. 15) sequences of fragment-2 are shown in FIG. 14. The nucleotide (SEQ ID No. 16) and amino acid (SEQ ID No. 17) sequences of fragment-3 are shown in FIG. 15. The nucleotide (SEQ ID No. 18) and amino acid (SEQ ID No. 19) sequences of fragment-4 are shown in FIG. 16. The nucleotide (SEQ ID No. 20) and amino acid (SEQ ID No. 21) sequences of fragment-5 are shown in FIG. 17. Using the cloning strategy detailed in Example 2 (above), we designed and prepared synthetic oligonucleotides (~30 bp in length) and used them in amplifying the various virB10 protein fragments. Table 4 shows the nucleotide sequence of the various oligonucleotides (i.e., SEQ ID Nos. 22-31) used in the PCR amplification reaction.

Figure 19:
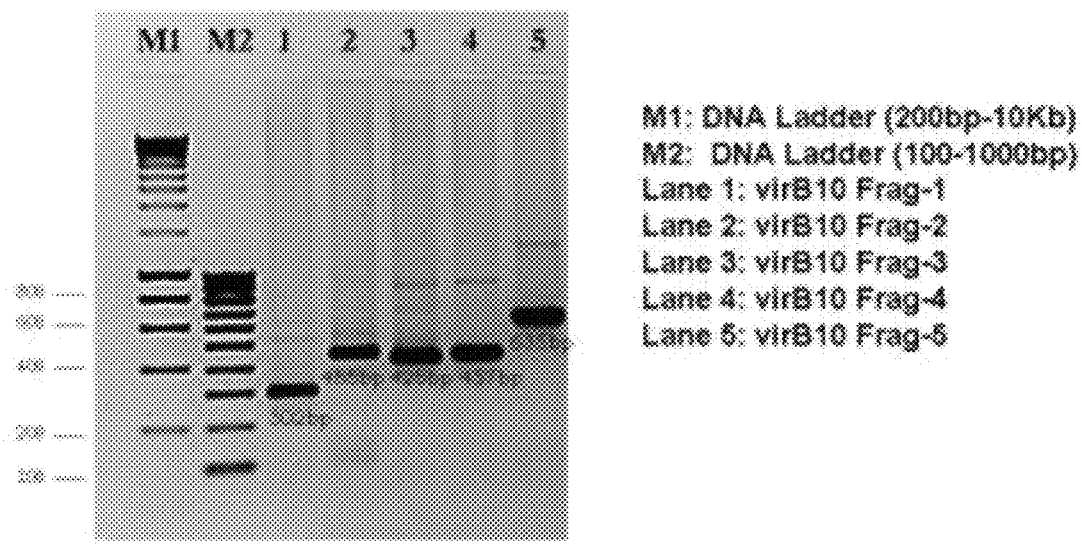
FIG. 19 depicts the EK/LIC PCR Amplification of *Anaplasma* TIVSS virB10 Fragments.
Figure 20:
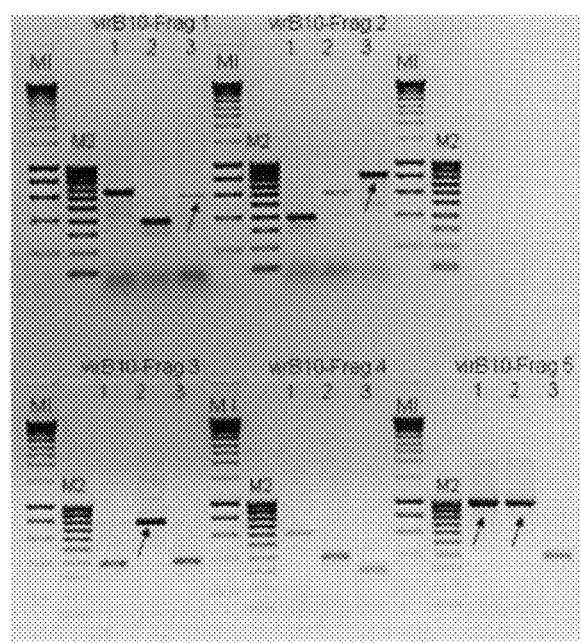
FIG. 20 depicts the Colony PCR of Fragments 1-3 Transformants in NOVABLUE *E. coli*.

Using the synthetic oligonucleotides (polynucleotide sequence listed in Table 4) and genomic DNA from *Anaplasma phagocytophilum*, we successfully amplified five (5) virB10 gene fragments; as well as a non-TIVSS gene (i.e., p44 proteins) (See, FIGS. 19 and 20).

FIG. 19 shows an agarose gel of the amplified virB10 fragments 1-5 prior to processing of the PCR reactions in preparation for ligation into pET30 vector. In preparation for ligation with the vector, the PCR amplification reactions were treated to remove any remaining nucleotides, primers, and reaction components. The resulting PCR products were then treated with T4 DNA polymerase and ligated into pET30 using standard protocols. Ligation of the virB10 fragment insert DNA (including succinate dehydrogenase iron-sulfur and p44 protein insert DNAs) was performed as described below.

II) T4 Polymerase Treatment of PCR Products and Ligation into pET30 Vector

Figure 22:
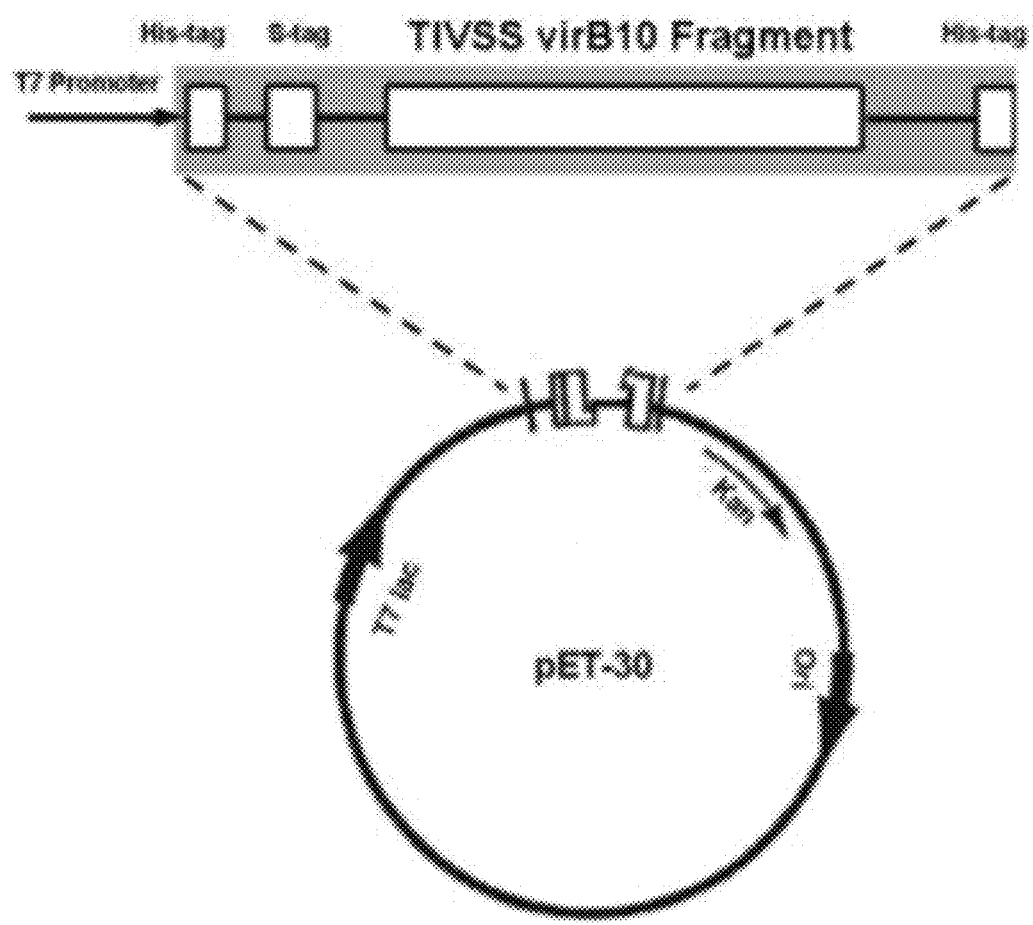
FIG. 22 depicts the pET-30 Vector Containing virB10 Gene Fragments.

In order to ligate the cloned fragment insert DNAs with the plasmid vector, it is necessary to create compatible ends between the amplicon and the chosen vector (e.g., pET30 Ek/LIC). We generated overhangs compatible with the Ek/LIC cloning vector on the insert DNA by T4 DNA polymerase treatment of the PCR amplicon. We ligated the treated amplicons into the expression vector to form pET30/insert DNA. FIG. 22 depicts the pET30 vector containing the insert DNA (Fragments 1-5).

III) Transformation of Recombinant Clones into NOVABLUE *E. coli*

In these series of experiments, we transformed the ligated DNAs (annealing reaction) into host bacterial cells (NOVABLUE *E. coli*). The ligated DNAs were virB10 fragments 1-5 amplicons. We chose NOVABLUE *E. coli* because this bacterial strain is optimized for producing a stable cell line containing a recombinant insert (see, NOVABLUE Ek/LIC manual). Transformation into NOVABLUE competent *E. coli* (Novagen) was performed using standard protocols. First, appropriate numbers of 20 µl aliquots of competent cells were prepared from −80° C., and allowed to thaw on ice for several minutes, followed by the addition of 1 µl of the annealing reaction and gentle stirring. The mixture was further incubated on ice for an additional 5 minutes, followed by heating the tubes for 30 seconds in a 42° C. water bath. The tubes were immediately placed on ice for 2 minutes. SOC (Super Optimal broth with Catabolite repression medium, containing 2% w/v bacto-tryptone, 0.5% w/v bacto-yeast extract, 10 mM NaCl, 2.5 mM KCl, 10 mM MgCl$_2$, 20 mM glucose) (at room temperature) was added into the tubes, and the reactions were further incubated for 1 hour at 37° C. with shaking (250 rpm). Cells were plated onto LB agar plates (containing kanamycin) and incubated at 37° C. overnight.

IV) Colony PCR of NOVABLUE Transformants

To confirm the successful transformation of insert DNA (pET30/insert DNA) in *E. coli* cells, we selected several colonies of each transformant grown on LB plates (with kanamycin), and performed colony PCR using the same set of Ek/LIC primers as in the amplification of the genes from the *Anaplasma* genomic DNA. An aliquot of each PCR reaction was analyzed using agarose gel electrophoresis.

Figure 21:
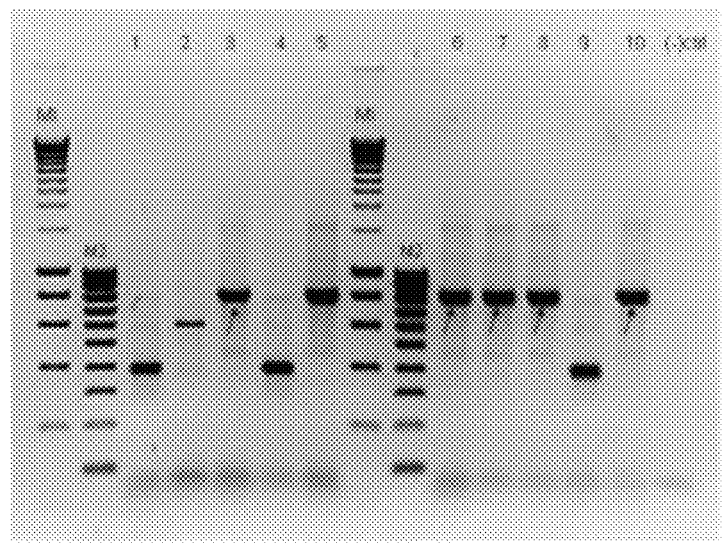
FIG. 21 depicts the Colony PCR of Fragment 4 Transformants in NOVABLUE *E. coli*.

FIG. 20 shows agarose gel electrophoresis analysis of three virB10 transformants for each fragment (1, 2, 3, and 5) in NOVABLUE *E. coli*. FIG. 21 shows agarose gel electrophoresis analysis of six virB10 transformants for fragment 4 (arrows). NOVABLUE *E. coli* colonies containing the pET30/insert DNA were further cultured in LB-kanamycin broth (for the isolation of plasmids).

V) Plasmid Mini-Preps

In order to confirm the presence and sequence accuracy of the cloned insert DNA in the pET30 vector, we performed sequence analysis on the recombinant plasmids. The sequence analysis also provides information that the insert was in-frame of the upstream His-tag sequence. First, we isolated plasmid DNA from the transformed *E. coli*. WIZARD Plus SV Minipreps DNA Purification system (PROMEGA) was used according to the manufacturer's recommended protocol. The concentration (1 OD$_{260/280}$=0.5 mg/ml) and the relative purity (OD$_{260/280}$) of the isolated plasmid DNA preparations were determined by spectrophotometric analysis.

VI) Sequencing Analysis of Insert DNA

We next performed sequence analysis on the isolated plasmid DNA using the APPLIED BIOSYSTEMS 3130 Genetic Analyzer DNA Sequencing instrument. All of the insert DNA were confirmed to be accurate by BLAST analysis and in-frame. BLAST (Basic Local Alignment Search Tool, url: <blast.ncbi.nlm.nih.gov/Blast.cgi>) analysis of the sequences confirmed a match between the nucleotide and deduced amino acid sequences for each of the fragments and the published sequences of the *Anaplasma phagocytophilum* virB10 gene.

VII) Transformation of BL21 (DE3) *E. coli* with Recombinant Plasmids

After confirmation of the obtained recombinant plasmids, we proceeded to transform them into BL21 (DE3) competent *E. coli* (Novagen). Transformation was carried out by removing the appropriate number of 20 µl aliquots of competent cells from −80° C., allowing the tubes to thaw on ice for several minutes, followed by the addition of 1 µl of the plasmid preparation to the cells with gentle stirring. The mixture was incubated on ice for 5 minutes, followed by heating of the tubes for exactly 30 seconds in a 42° C. water bath. The tubes were immediately placed on ice for 2 min. SOC (room temperature) was added, and the reactions were further incubated at 37° C. for 1 hour at 250 rpm. Cells were then plated onto LB agar plated (containing kanamycin) and incubated at 37° C. overnight.

VIII) Colony PCR of BL21 (DE3) Transformants

To confirm the successful transformation of recombinant pET30/insert DNA in BL21 (DE3) *E. coli* cells, we selected several colonies of each transformant grown on LB plates (with kanamycin), and performed colony PCR using forward and reverse vector-specific primers. An aliquot of each PCR reaction was analyzed using agarose gel electrophoresis. Amplicons of expected size for each fragment were observed following analysis of the PCR reactions (data not shown).

Example 5

Expression and Purification of virB10 Protein Fragments

I) Expression of Recombinant virB10 fragments 1-5 in *E. coli*

In order to express fragments 1-5 of virB10, the Overnight Express™ Autoinduction System 1 (Novagen) was used. In each 500 ml flask (one baffled and one flat bottom per fragment), 110 ml of LB broth was added. From the Autoinduction kit, 0.02 volume of OnEx™ Solution 1, 0.05 volume of OnEx Solution 2, and 0.001 volume of OnEx Solution 3 were added to 1 volume LB medium (glucose free). Kanamycin was added to a final concentration of 30 µg/ml. LB medium was inoculated with isolated colonies from the plates, and incubated overnight (approximately 16 hours) at 37° C. with shaking at 250 rpm.

The following day, each culture of the fragments was spun down for 10 minutes at 10,000×g. The supernatant was decanted, and 15 ml of BUGBUSTER Master Mix (Novagen) was used to resuspend each pellet thoroughly. The cell suspension was incubated in room temperature on a shaker at slow speed for 20 minutes, and was then centrifuged at 4° C. at 16,000×g for 20 minutes to separate the soluble cytoplasmic fraction (supernatant) from the insoluble cytoplasmic fraction (pellet). The pellets were resuspended in 15 ml BUGBUSTER, after which 6 volumes of 1:10 diluted BUGBUSTER was added to each and then vortexed for 1 minute. The resuspension was centrifuged at 4° C. at 5,000×g for 15 minutes, and the supernatant was saved as an insoluble wash. The pellet was resuspended in half the original culture volume of 1:10 diluted BUGBUSTER, mixed by vortexing, and centrifuged at 4° C. at 5,000×g for 15 minutes. This step was repeated twice, with the final spin at 16,000×g. The pellets (inclusion bodies) were then kept at −70° C. until needed for further purification.

Figure 23:
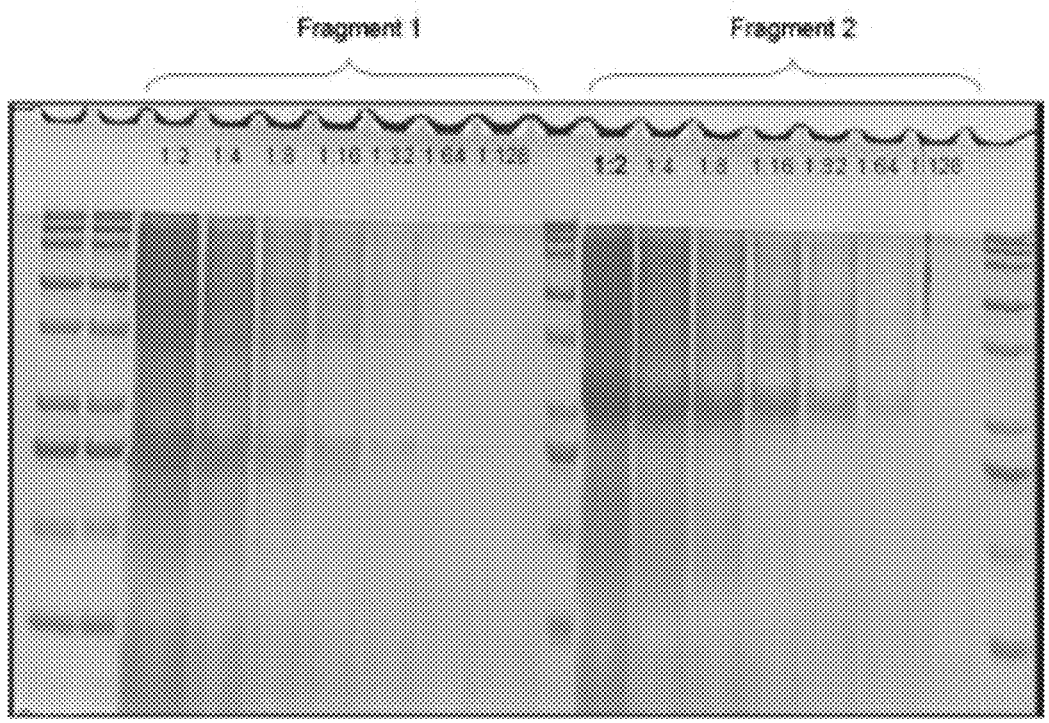
FIG. 23 depicts the Presence of Fragments 1 and 2 in the Soluble Fraction following Induction of Expression.
Figure 24:
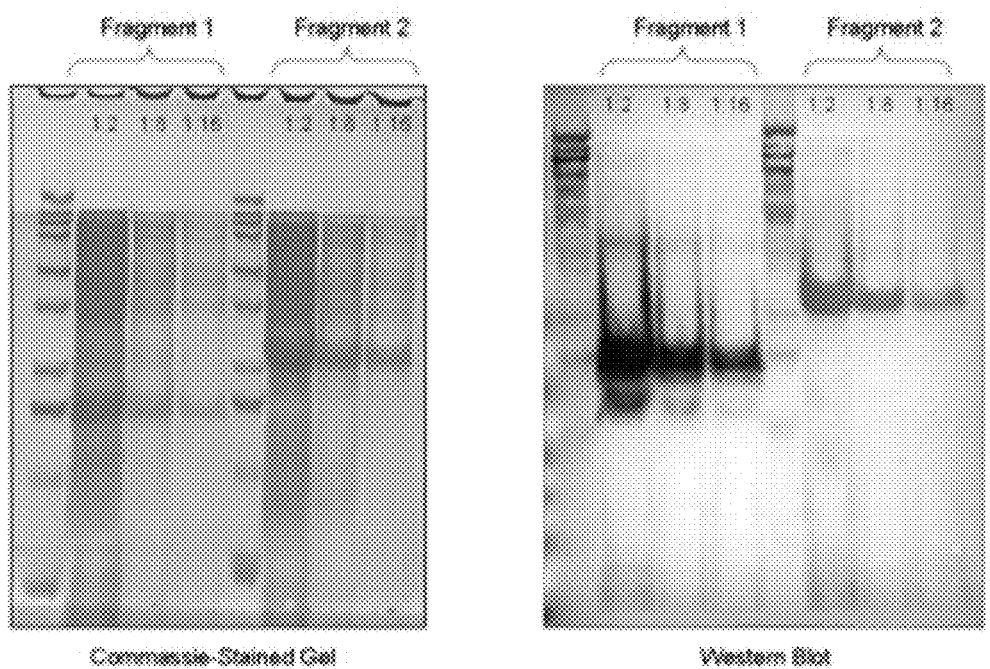
FIG. 24 depicts the COOMASSIE-Stained Gel and His-Tag Western Blot of Fragments 1 and 2.
Figure 26:
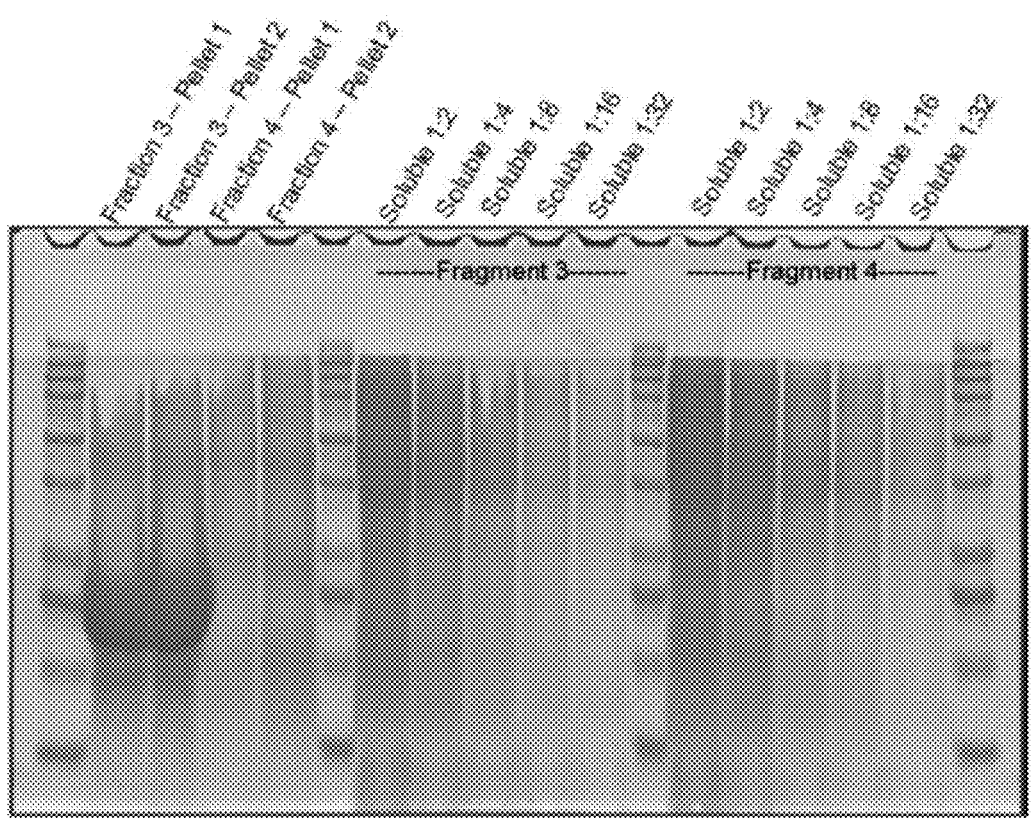
FIG. 26 depicts the Induction of Fragments 3 and 4. This figure shows the Presence of Fragments 3 and 4 in the Insoluble Fraction.
Figure 27:
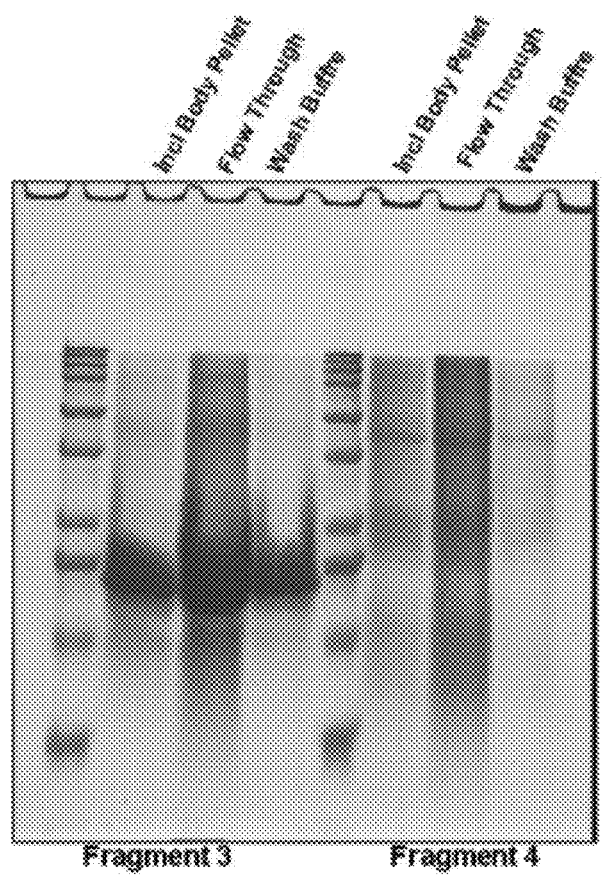
FIG. 27 depicts the Purification of the Inclusion Body Fraction
Figure 29:
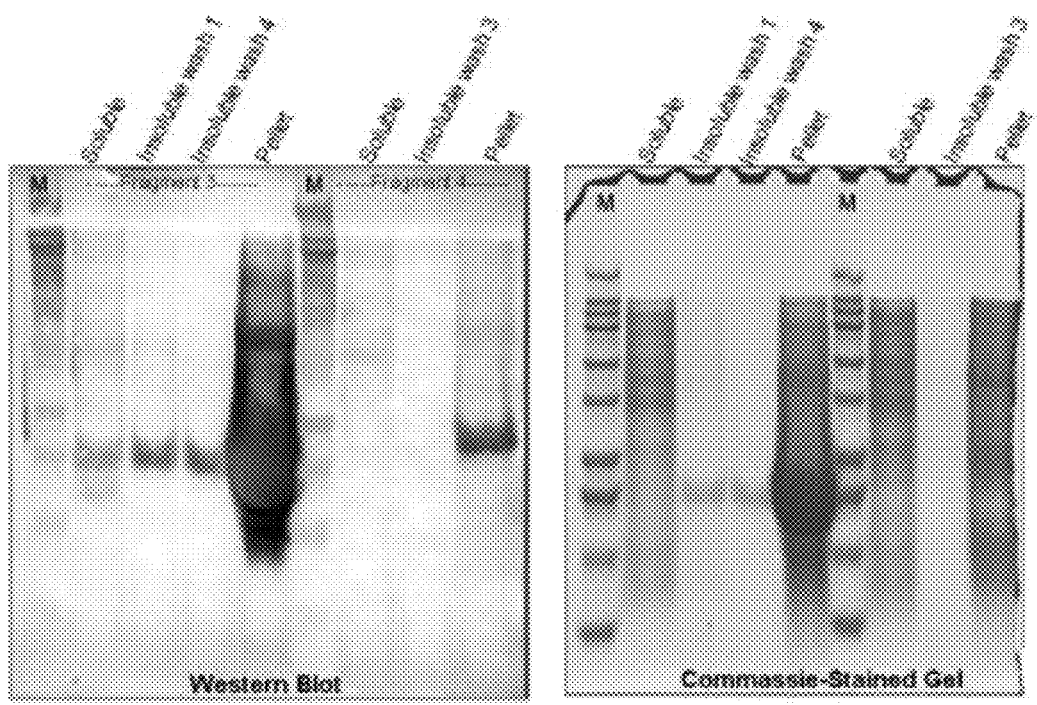
FIG. 29 depicts the COOMASSIE-Stained Gel and His-Tag Western Blot of Fragments 3 and 4.
Figure 30:
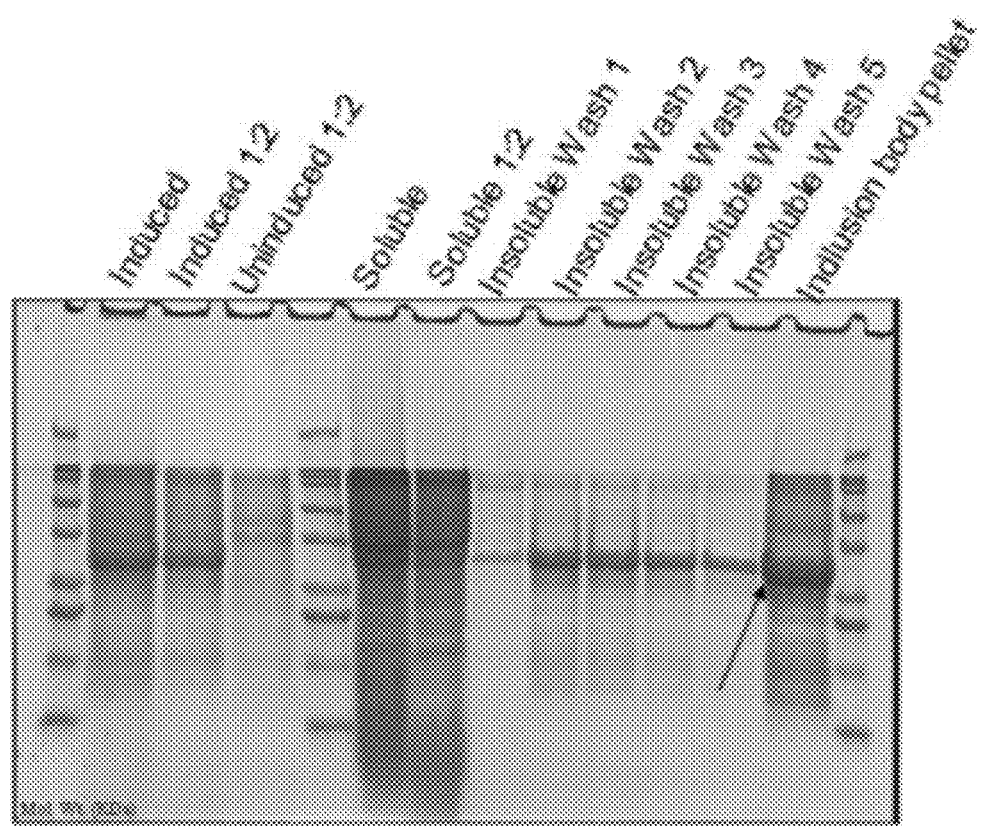
FIG. 30 depicts the Induction of Fragment 5. The arrow shows the presence of the Induced protein in the Insoluble (Inclusion Body) Fraction.
Figure 31:
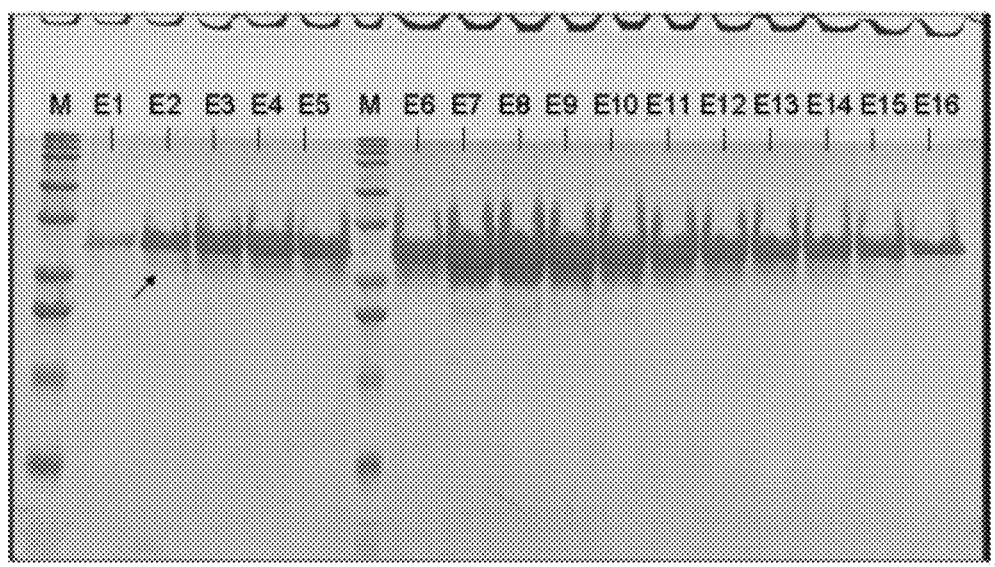
FIG. 31 depicts the Nickel Column Purification of Fragment 5.
Figure 32:
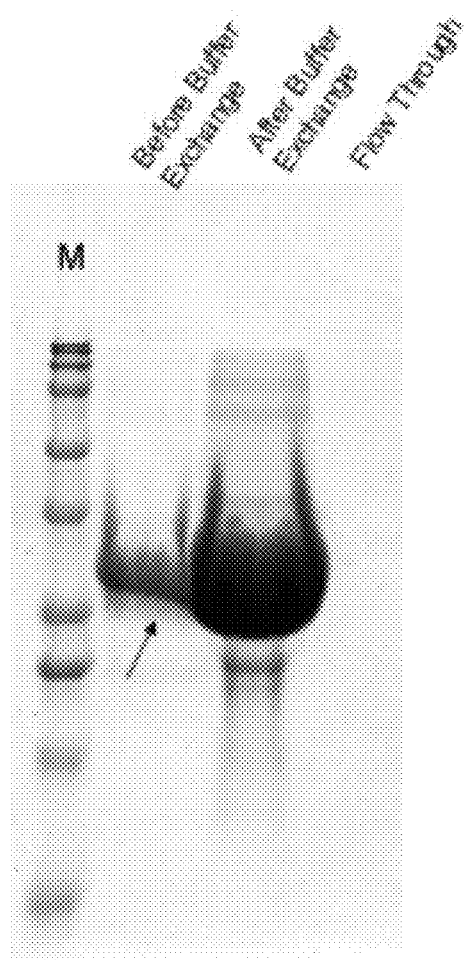
FIG. 32 depicts the His-Tag Western Blot of Fragment 5.

The soluble cytoplasmic fractions and the insoluble washes were analysed on SDS-PAGE gels, which showed that fragments 1 and 2 were found in the soluble fractions (FIG. 23), and fragments 3-5 were present in the insoluble (inclusion body) fractions (FIGS. 26, 27, 30). A COOMASSIE-stained gel and Western blot detection of fragments 1 and 2 using an antibody directed against the 6×His-tag shows that a these recombinant proteins were present in the soluble fraction (FIG. 24). A COOMASSIE-stained gel and Western blot detection of fragments 3, 4, and 5 using an antibody directed against the 6×His-tag shows that a majority of these recombinant proteins was present in the insoluble (inclusion body) fraction (FIGS. 29 and 32).

Figure 25:
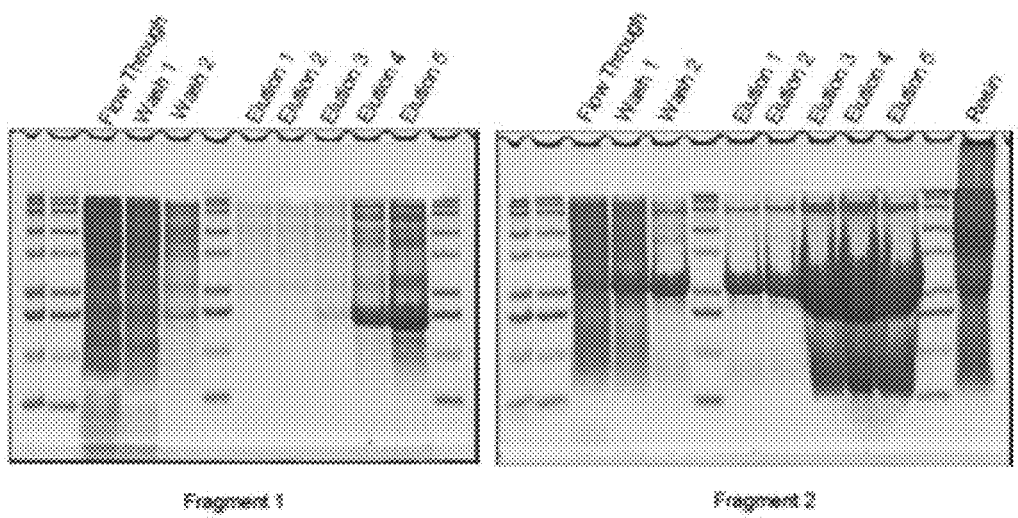
FIG. 25 depicts the Nickel Column Purification of Fragments 1 and 2.

For purification of fragments 1 and 2 from the soluble fraction, Ni-NTA Buffer Kit (Novagen) and Ni-NTA His•Bind Resin (Novagen) were used. In order to equilibrate the resin, 30 ml 1× Binding Buffer (equal to the amount of the soluble fraction) was added to 5 ml resin, and the mixture was incubated on a shaker in 4° C. for 10 min, prior to the tubes being placed in an upright position at room temperature to facilitate the settling of the resin at the bottom of the tubes. 30 ml of the Binding Buffer from the top was taken out and replaced with the soluble fraction. The resin/soluble fraction mixture was then incubated on a shaker at 4° C. for 1 hour. The mixture was then decanted into an empty column. Using a slow drip, the flow-through was collected. Taking careful steps to avoid allowing the resin to become dry at any time, 4 ml or 1× Wash buffer was added twice. Lastly, 5×0.5 ml of 1× Elution Buffer was added to the resin to collect the protein. The flow-through, wash buffers and elution buffers were analyzed on an SDS-PAGE gel to confirm the successful purification of the proteins, and to determine in which fractions the proteins were eluted. SDS PAGE analysis confirmed that a majority of recombinant fragment-1 and 2 eluted from the column in elution fractions 1-3 (FIG. 25).

Figure 28:
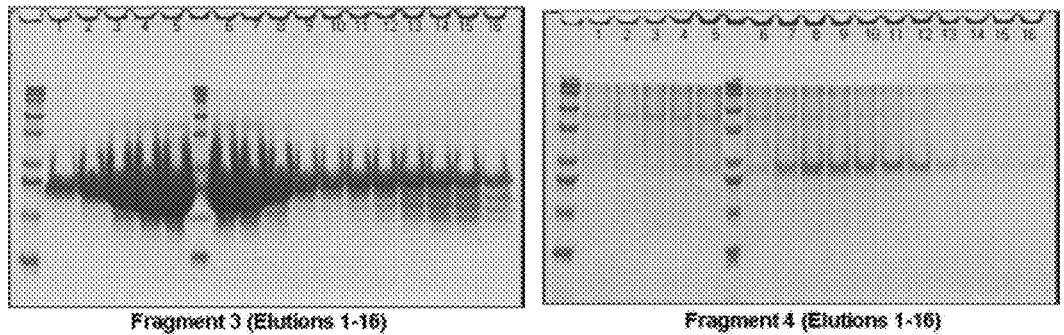
FIG. 28 depicts the Nickel Column Purification of Fragments 3 and 4 from the Inclusion Body Fraction.

II) Purification of Recombinant virB10 Fragments 3, 4, and 5 under Urea Denaturing Conditions The inclusion body fractions containing recombinant fragments 3-5 were purified under urea denaturing conditions as previously described for full-length virB10 and p44 proteins using freshly prepared buffers containing urea. Nickel column purification of fragments 3 and 4 is shown in FIG. 28.

Example 6 IgG/IgM ELISA for Recombinantly Expressed virB10 Protein Fragments

We performed IgG and IgM ELISA assays and evaluated the binding activity of the recombinant virB10 protein fragments towards IgM and/or IgG.

Patient Study: virB10 Protein Fragments 1-5
virB10 Protein Fragments 1 and 2

In these studies, we examined recombinant virB10 fragments 1 and 2 in IgG ELISAs. Fragment 1 exhibited a dose-dependent increase in binding towards IgG sero-positive serum (as measured by $OD_{450}$ nm). IgG ELISA for recombinant fragment 1 attained a 76.2% sensitivity (FIG. 33) and 71.4% specificity, both of which satisfies the threshold ($\geq$70%) required by industry.

Figure 33:
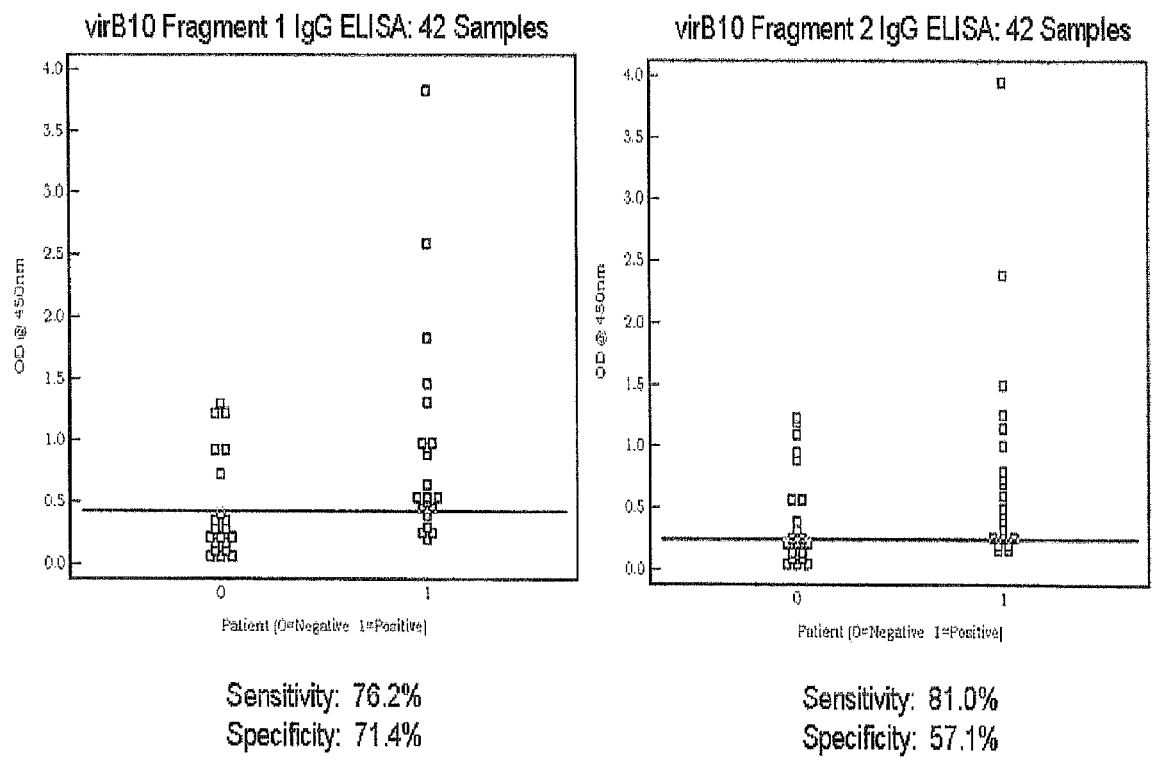
FIG. 33 depicts the IgG ELISA for Recombinant virB10 Fragments 1 and 2.

Fragment 2 exhibited a dose-dependent increase in binding towards IgG sero-positive serum (as measured by $OD_{450}$ nm). IgG ELISA for recombinant fragment 1 attained a 81.0% sensitivity (FIG. 33). However, the specificity attained of 57.1%.

Figure 34:
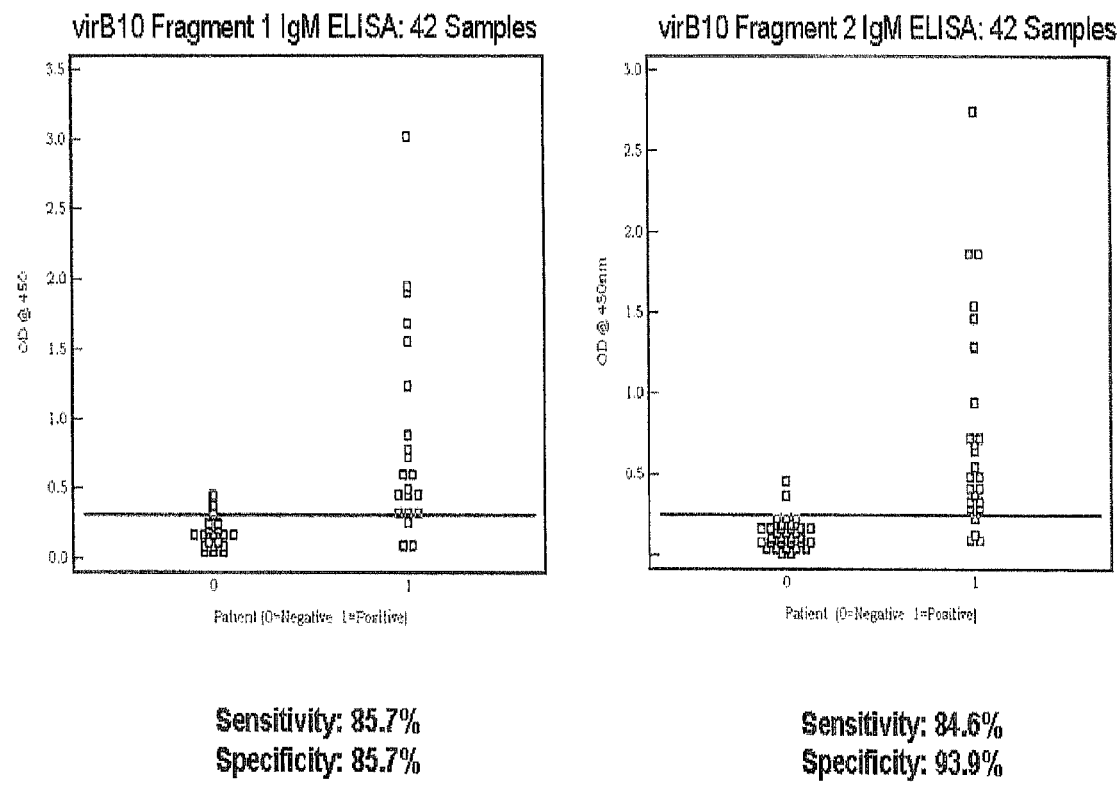
FIG. 34 depicts the IgM ELISA for Recombinant virB10 Fragments 1 and 2.

Recombinant fragment 1, when tested in an IgM ELISA, exhibited a dose-dependent increase in binding towards IgM sero-positive serum as measured by $OD_{450}$ nm. IgM ELISA for recombinant fragment 1 attained a 85.6% sensitivity (FIG. 34) and 85.6% specificity.

Recombinant fragment 2 when tested in an IgM ELISA, exhibited a dose-dependent increase in binding towards IgM sero-positive serum as measured by $OD_{450}$ nm. IgM ELISA for recombinant fragment 1 attained a 84.6% sensitivity (FIG. 34) and 93.9% specificity.

Combined virB10 Protein Fragments 1 and 2

Figure 35:
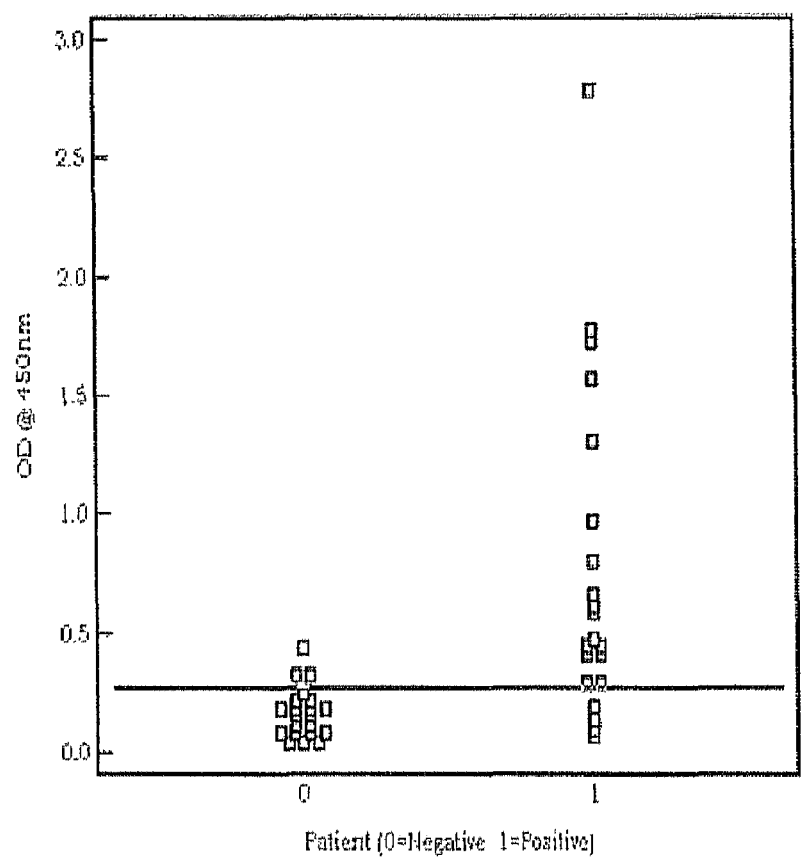
FIG. 35 depicts the IgM ELISA Analysis for Combined virB10 Fragments 1 and 2.

In the next series of experiments, we sought to test the usefulness of combining fragments 1 and 2. Recombinant fragments 1 and 2, when combined and used for ELISA analysis, exhibited a dose-dependent increase in binding towards IgM sero-positive serum as measured by $OD_{450}$ nm. As shown in FIG. 35, the combination of fragments 1 and 2 attained an 81.0% sensitivity and 85.7% specificity.

Figure 36:
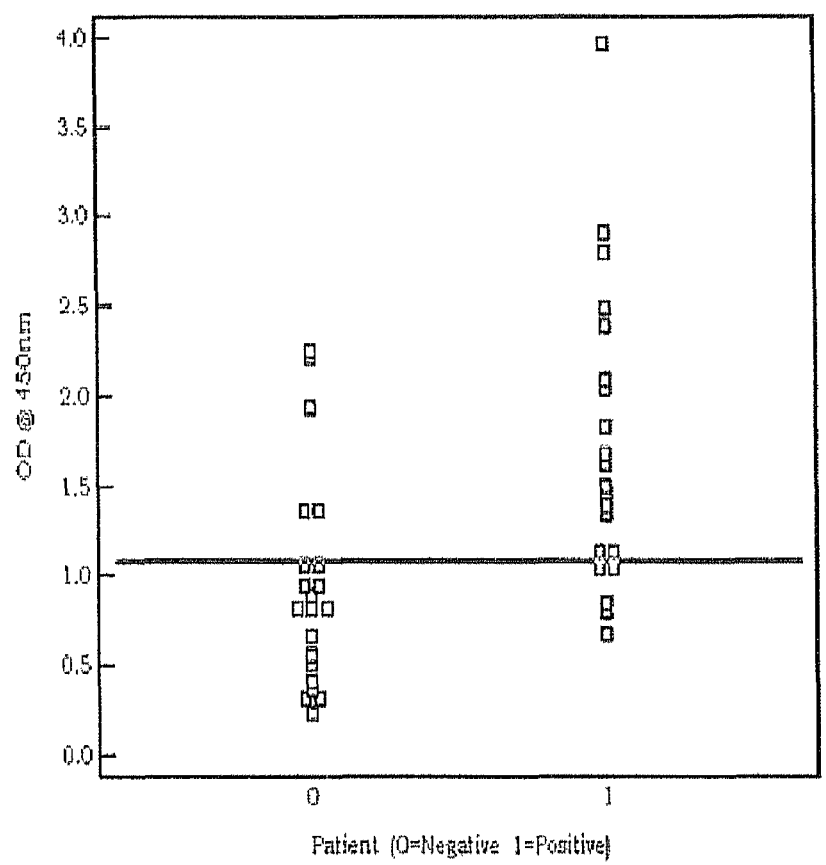
FIG. 36 depicts the IgG ELISA Analysis for Combined virB10 Fragments 1 and 2.

Recombinant fragments 1 and 2, when combined and used for ELISA analysis, exhibited a dose-dependent increase in binding towards IgG sero-positive serum as measured by $OD_{450}$ nm. As shown in FIG. 36, the use of a combination of fragments 1 and 2 attained ELISA with 76. % sensitivity and 76.2% specificity.

virB10 Protein Fragments 3 and 4

In the next series of studies, we examined recombinant virB10 fragments 3 and 4 in IgG ELISAs. Fragment 3 exhibited a dose-dependent increase in binding towards IgG sero-positive serum (as measured by $OD_{450}$ nm). IgG ELISA for recombinant fragment 3 attained a 85.7% sensitivity (FIG. 37) and a specificity of 61.9%.

Fragment 4 exhibited a dose-dependent increase in binding towards IgG sero-positive serum (as measured by $OD_{450}$ nm). IgG ELISA for recombinant fragment 4 attained a 81.0% sensitivity (FIG. 37) and the specificity of 61.9%.

virB10 Protein Fragment 5

Figure 38:
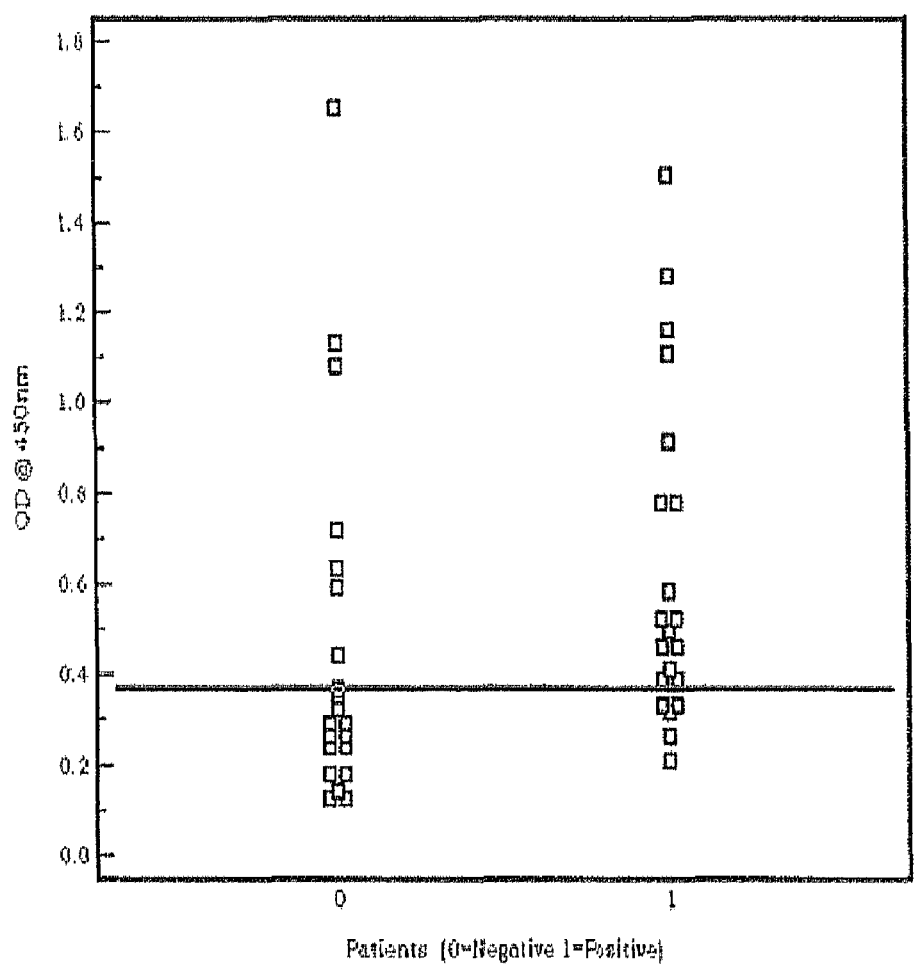
FIG. 38 depicts the IgG ELISA for Recombinant virB10 Fragment 5.

In the final series of studies, we examined recombinant virB10 fragments 5 in IgG ELISAs. Fragment 5 exhibited a dose-dependent increase in binding towards IgG sero-positive serum (as measured by $OD_{450}$ nm). IgG ELISA for recombinant fragment 3 attained 76.2% sensitivity (FIG. 38) and a specificity of 66.7%.

EXPERIMENTAL PROTOCOL

*Anaplasma* IgG ELISA
1. Antigen coating concentration 0.5 µg/ml in carbonate buffer (pH 9.6) (100 µl per well). Coating overnight in 4° C.
2. Wash three time in PBST buffer (0.5% TWEEN-20)
3. Block with 200 µl blocker buffer (casein in PBS, Thermo Sci. #37528). Incubate for 1 hour in room temperature
4. Wash three times with PBST buffer (0.5% TWEEN-20)
5. Add 100 µl 1:200 diluted human sera (dilution buffer: 1:20 casein buffer in PBST). Incubate for 1 hour in room temperature
6. Wash four times with PBST buffer (0.5% TWEEN-20)
7. Add goat anti-human IgG antibody (1:15,000 diluted in casein dilution buffer (1:20 casein buffer in PBST). Incubate for 1 hour in room temperature
8. Wash four times with PBST buffer (0.5% TWEEN-20)
9. Add 100 µl TBM substrate. Incubate in room temperature for 3 minutes
10. Stop the reaction with 2N HCl
11. Read the result at $OD_{450}$

*Anaplasma* IgM ELISA
1. Antigen coating concentration 0.125 µg/ml in carbonate buffer (pH 9.6) (100 µl per well). Coating overnight in 4° C.
2. Wash three time in PBST buffer (0.5% TWEEN-20)
3. Block with 200 µl blocker buffer (casein in PBS, Thermo Sci. #37528). Incubate for 1 hour in room temperature
4. Wash three times with PBST buffer (0.5% TWEEN-20)
5. Dilute human sera in GullSorb™ (1:10) to prepare mixture 1. Incubate in room temperature for 5 minutes. Dilute incubated mixture 1 in sample dilution buffer (1:20 casein buffer in PBST). Therefore, the total dilution factor for human sera is 1:100
6. Add 100 µl 1:100 diluted human sera to the plate. Incubate for 1 hour in room temperature
7. Wash four times with PBST buffer (0.5% TWEEN-20)
8. Add goat anti-human IgM antibody (1:10,000 diluted in casein dilution buffer (1:20 casein buffer in PBST). Incubate for 1 hour in room temperature
9. Wash four times with PBST buffer (0.5% TWEEN-20)
10. Add 100 µl TBM substrate. Incubate in room temperature for 3 minutes
11. Stop the reaction with 2N HCl
12. Read the result at $OD_{450}$ All publications and patents cited in this specification are herein incorporated by reference in their entirety. Various modifications and variations of the described composition, method, and systems of the invention will be apparent to those skilled in the art without departing from the scope and spirit of the invention. Although the invention has been described in connection with specific preferred embodiments and certain working examples, it should be understood that the invention as claimed should not be unduly limited to such specific embodiments. Various modifications of the above-described modes for carrying out the invention that are obvious to those skilled in the filed of molecular biology, recombinant expression and related fields are intended to be within the scope of the following claims.

TABLE 1

Oligonucleotide Sequences Used in Gene Amplification for *Anaplasma phagocytophilum* Encoding virB10 and Non-TIVSS Protein Components

| Recombinant TIVSS & Non-TIVSS Protein | NCBI Accession # | Oligonucleotides | Gene Amplification |
|---|---|---|---|
| virB10 | YP_505896 | Fwd: 5'-gacgacgacaagatggctgacgaaataaggggttc-3' (SEQ. ID No. 1)<br>Rev: 5'-gaggagaagcccggtctacctcaccgcatcacg-3' (SEQ. ID No. 2) | Yes |
| Succinate Dehydrogenase, iron-sulfur subunit | YP_504786 | Fwd: 5'-gacgacgacaagatggtgcagttttctttgcc-3' (SEQ. ID No. 3)<br>Rev: 5'-gaggagaagcccggtctagagctccaatccttttatc-3' (SEQ. ID No. 4) | Yes |
| p44-8 Outer Membrane Protein | YP_504769 | Fwd: 5'-gacgacgacaagatgctaaggctcatggtgatgg -3' (SEQ ID No: 5)<br>Rev: 5'-gaggagaagcccggttcaaaaacgtattgtgcgacg-3' (SEQ ID No: 6) | Yes |

TABLE 2

Recombinant Expression of virB10 and Non-TIVSS Proteins in *Anaplasma phagocytophilum*

| Recombinant TIVSS and Non-TIVSS Protein | NCBI Accession Nos. | Recombinant Expression |
|---|---|---|
| virB10 | YP_505896 (SEQ ID No. 7) | Yes |
| Succinate Dehydrogenase, iron-sulfur subunit | YP_504786 (SEQ ID No. 8) | No |
| P44-8 Outer Membrane Protein | YP_504769 (SEQ ID No. 9) | Yes |

TABLE 3

IgM/IgG ELISA Assay for Recombinant virB10 and p44

| Recombinant TIVSS and Non-TIVSS Proteins | IgM ELISA | IgG ELISA |
|---|---|---|
| virB10 | Sensitivity = 71.4%<br>Specificity = 85.7% | Sensitivity = 57.1%<br>Specificity = 76.2% |
| p44 Outer Membrane Protein | Sensitivity = 81%<br>Specificity = 90.5% | Sensitivity = 42%-71.4%<br>Specificity = 71.4%-100% |

TABLE 4

Primers for Generation of Polynucleotides Encoding Five (5) Recombinant Protein Fragments of TIVSS virB10 in *Anaplasma phagocytophilum*

| TIVSS virB10 Fragments | Primers | Nucleotide Sequences |
|---|---|---|
| Fragment 1 | Forward | 5'-gacgacgacaagatgatggctgacgaaataag-3' SEQ ID NO: 22 |
|  | Reverse | 5'-gaggagaagcccggttatggcgtcaagattct-3' SEQ ID NO: 23 |
| Fragment 2 | Forward | 5'-gacgacgacaagatgcagattcctcgtgttat-3' SEQ ID NO: 24 |
|  | Reverse | 5'-gaggagaagcccggttattccttcccgccaac-3' SEQ ID NO: 25 |
| Fragment 3 | Forward | 5'-gacgacgacaagatggaagatgctcggtttac-3' SEQ ID NO: 26 |
|  | Reverse | 5'-gaggagaagcccggttagcccactttattatc-3' SEQ ID NO: 27 |
| Fragment 4 | Forward | 5'-gacgacgacaagatgttacctcatggcgttga-3' SEQ ID NO: 28 |
|  | Reverse | 5'-gaggagaagcccggttactacctcaccgcatc-3' SEQ ID NO: 29 |
| Fragment 5 | Forward | 5'-gacgacgacaagatgccgcttgtaatgcctac-3' SEQ ID NO: 30 |
|  | Reverse | 5' gaggagaagcccggttataaaatgaccctgga-3' SEQ ID NO: 31 |

TABLE 5

ELISA Sensitivity and Specificity for Various virB10 Protein Fragments

| Recombinant TIVSS virB10 Fragments | IgG ELISA | IgM ELISA |
|---|---|---|
| Fragment 1 | Sensitivity = 76.2%<br>Specificity = 71.4% | Sensitivity = 85.7%<br>Specificity = 85.7% |
| Fragment 2 | Sensitivity = 81.0%<br>Specificity = 57.1% | Sensitivity = 84.6%<br>Specificity = 93.9% |
| Fragments 1 + 2 | Sensitivity = 76.2%<br>Specificity = 76.2% | Sensitivity = 81.0%<br>Specificity = 85.7% |
| Fragment 3 | Sensitivity = 85.7%<br>Specificity = 61.9% | Not determined |
| Fragment 4 | Sensitivity = 81.0%<br>Specificity = 61.9% | Not determined |
| Fragment 5 | Sensitivity = 76.2%<br>Specificity = 66.7% | Not determined |

What is claimed is:

1. An isolated polypeptide, wherein said isolated polypeptide is an amino acid sequence selected from the group consisting of SEQ ID NO: 13 and SEQ ID NO: 15.

2. The isolated polypeptide of claim 1, wherein said isolated polypeptide consists of the amino acid sequence of SEQ ID NO: 13.

3. The isolated polypeptide of claim 1, wherein said isolated polypeptide consists of the amino acid sequence of SEQ ID NO: 15.

4. A composition comprising the isolated polypeptide of claim 1 and an inert support.

5. The composition of claim 4, wherein said inert support is selected from the group consisting of polyethylene, polypropylene and glass.

6. The composition of claim 4, wherein said inert support is a microtiter well.

7. An article of manufacture comprising a packaging material and the isolated polypeptide of claim 1.

8. The article of manufacture of claim 7, wherein said packaging material comprises an instruction for detecting the presence of antibody against *Anaplasma phagocytophilum*.

9. A method of producing the isolated polypeptide of claim 1, comprising the steps of:
   (i) introducing an isolated polynucleotide into a host cell, wherein said isolated polynucleotide has a nucleotide sequence selected from the group consisting of SEQ ID NO. 12 and SEQ ID NO: 14;
   (ii) growing said host cell in a culture medium under suitable conditions to permit production of said polypeptide and
   (iii) isolating said isolated polypeptide.

10. The method of claim 9, wherein said polynucleotide has the nucleotide sequence set forth in SEQ ID NO: 12 and said isolated polypeptide consists of the amino acid set forth in SEQ ID NO: 13.

11. The method of claim 9, wherein said polynucleotide has the nucleotide sequence set forth in SEQ ID NO: 14 and said isolated polypeptide consists of the amino acid set forth in SEQ ID NO: 15.

* * * * *